US010617683B2

(12) United States Patent
Zhou et al.

(10) Patent No.: US 10,617,683 B2
(45) Date of Patent: Apr. 14, 2020

(54) INHIBITORS OF CRL4 UBIQUITIN LIGASE AND USES THEREOF

(71) Applicant: Cornell University, Ithaca, NY (US)

(72) Inventors: Pengbo Zhou, Princeton Junction, NJ (US); J. David Warren, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/422,571

(22) PCT Filed: Aug. 21, 2013

(86) PCT No.: PCT/US2013/056009
§ 371 (c)(1),
(2) Date: Feb. 19, 2015

(87) PCT Pub. No.: WO2014/031759
PCT Pub. Date: Feb. 27, 2014

(65) Prior Publication Data
US 2015/0196546 A1   Jul. 16, 2015

Related U.S. Application Data

(60) Provisional application No. 61/691,539, filed on Aug. 21, 2012.

(51) Int. Cl.
*A61K 31/4709* (2006.01)
*A61K 31/382* (2006.01)
*A61K 31/39* (2006.01)
*A61K 31/4196* (2006.01)
*A61K 31/425* (2006.01)
*A61K 31/506* (2006.01)
*A61K 31/519* (2006.01)
*A61K 31/4704* (2006.01)
*A61K 31/423* (2006.01)
*A61K 31/426* (2006.01)
*A61K 31/44* (2006.01)
*A61K 31/496* (2006.01)
*A61K 31/4985* (2006.01)
*A61K 45/06* (2006.01)

(52) U.S. Cl.
CPC ........ *A61K 31/4709* (2013.01); *A61K 31/382* (2013.01); *A61K 31/39* (2013.01); *A61K 31/4196* (2013.01); *A61K 31/423* (2013.01); *A61K 31/425* (2013.01); *A61K 31/426* (2013.01); *A61K 31/44* (2013.01); *A61K 31/4704* (2013.01); *A61K 31/496* (2013.01); *A61K 31/4985* (2013.01); *A61K 31/506* (2013.01); *A61K 31/519* (2013.01); *A61K 45/06* (2013.01)

(58) Field of Classification Search
CPC .. A61K 31/4709; A61K 31/382; A61K 31/39; A61K 31/4196; A61K 31/423; A61K 31/425; A61K 31/426; A61K 31/44; A61K 31/4704; A61K 31/496; A61K 31/4985; A61K 31/506; A61K 31/519; A61K 45/06

See application file for complete search history.

(56) References Cited

U.S. PATENT DOCUMENTS

| | | | |
|---|---|---|---|
| 5,587,150 A | 12/1996 | Deflandre et al. | |
| 5,770,183 A | 6/1998 | Linares | |
| 6,033,649 A | 3/2000 | Gonzenbach et al. | |
| 8,513,181 B2 | 8/2013 | Zhou | |
| 2004/0198716 A1* | 10/2004 | Arad et al. | 514/212.03 |
| 2009/0163545 A1 | 6/2009 | Goldfarb | |
| 2010/0087415 A1* | 4/2010 | Whitten | A61K 31/397 514/210.02 |
| 2011/0044921 A1 | 2/2011 | Zhou | |
| 2011/0104186 A1 | 5/2011 | Valiante et al. | |

FOREIGN PATENT DOCUMENTS

| | | | |
|---|---|---|---|
| CN | 102282162 A | 12/2011 | |
| WO | WO 2009/134883 A1 | 11/2009 | |
| WO | WO2009134883 | * 11/2009 | ............. C07K 14/47 |

OTHER PUBLICATIONS

Fraile et al. (Oncogene (2012) 31, 2373-2388).*
Cannon, "Analog Design" in Burger's Medicinal Chemistry and Drug Discovery, 6th ed. 2003, Wiley, pp. 687-714.*
Hegenrother (Current Opinion in Chemical Biology 2006, 10: p. 213-218).*
Chembridge (Chembridge screening compound description / PubChem SID 3304582 Chembridge screening library compound establishing available date Jul. 28, 2005).*
Abbas et al.,"PCNA-dependent regulation of p21 ubiquitylation and degradation via the CRL4Cdt2 ubiquitin ligase complex",*Genes & Development*, 22: 2496-2506 (2008).
Abbas et al., "CRL1-FBXO11 Promotes Cdt2 Ubiquitylation and Degradation and Regulates Pr-Set7/Set8-Mediated Cellular Migration", *Molecular Cell*, 49(6): 1147-1158 (2013).
Angers et al.,"Molecular architecture and assembly of the DDB1-CUL4A ubiquitin ligase machinery", *Nature*, 443: 590-593 (2006).
Cang et al., "Deletion of DDB1 in Mouse Brain and Lens Leads to p53-Dependent Elimination of Proliferating Cells", *Cell*, 127:929-940 (2006).
Centore et al., "CRL4 Cdt2-Mediated Destruction of the Histone Methyltransferase Set8 Prevents Premature Chromatin Compaction in S Phase", *Molecular Cell*, 40(1): 22-33 (2010).

(Continued)

*Primary Examiner* — Robert H Havlin
(74) *Attorney, Agent, or Firm* — Leydig, Voit & Mayer, Ltd.

(57) ABSTRACT

The invention is directed to a method of treating a cancer in an animal and a method of increasing DNA repair activity in an animal. The methods comprise administering to an animal in need thereof an effective amount of a small molecule substance that interferes with the activity of CUL4A, such as a 1,3-benzoxathiol-2-one compound, a pyridine thione compound, a 2,6-diamino-4-thiopyran-3,5-dicarbonitrile compound, or a 1,2,4-triazole-3-thiol compound.

9 Claims, 25 Drawing Sheets

(56) References Cited

OTHER PUBLICATIONS

Chang et al., "DDB2 is a novel AR interacting protein and mediates AR ubiquitination/degradation", *The International Journal of Biochemistry & Cell Biology*, 44(11): 1952-1961 (2012).
Chen et al.,"The Human Homologue for the *Caenorhabditis elegans* cul-4 Gene is Amplified and Overexpressed in Primary Breast Cancers", *Cancer Research*, 58: 3677-3683 (1998).
Chen et al., "UV-damaged DNA binding proteins are targets of Cul4A-mediated ubiquitination and degradation", *J. Biol.Chem.*, 276: 48175-48182 (2001).
Chen et al., "A Kinase-Independent Function of c-Abl in Promoting Proteolytic Destruction of Damaged DNA Binding Proteins", *Molecular Cell*, 22(4): 489-99 (2006).
Dohna et al.,"Adrenocortical Carcinoma is Characterized by a High Frequency of Chromosomal Gains and High-Level Amplifications", *Genes Chromosomes & Cancer*, 28: 145-152 (2000).
Elgemeie et al., "A Total Synthesis of a New Class of Biazine Thioglycosides", *Journal of Carbohydrate Chemistry*, 23(8-9): 465-481 (2004).
Elnagdi et al., " Studies on Alkylheteroaromatic Compounds. The Reactivity of Alkyl Polyfunctionally Substituted Azines Towards Electrophilic Reagents", *Tetrahedron*, 45(11): 3597-3604 (1989).
Fan et al., "MWI-promoted preparation of 4H-thiopyran derivatives through one-pot multi-component reactions", *Journal of Chemical Research*, 12: 693-695 (2007).
He et al.,"DDB1 functions as a linker to recruit receptor WD40 proteins to CUL4-ROC1 ubiquitin ligases", *Genes & Development*, 20: 2949-2954 (2006).
Higa et al.,"CUL4-DDB1 ubiquitin ligase interacts with multiple WD40-repeat proteins and regulates histone methylation", *Nature Cell Biology*, 8(11): 1277-1283 (2006).
Hu et al., "WD40 protein FBW5 promotes ubiquitination of tumor suppressor TSC2 by DDB1-CUL4-ROC1 ligase", *Genes & Development*, 22(7): 866-871 (2008).
Huh et al., "CRL4CDT2 Targets CHK1 for PCNA-Independent Destruction", *Molecular & Cellular Biology*, 33(2): 213-226 (2013).
Hung et al., "Cul4A is an oncogene in malignant pleural mesothelioma", *J. Cell. Mol. Med.*, 15(2): 350-358 (2011).
Ito et al., "Identification of a primary target of thalidomide teratogenicity", *Science* 327, 1345-1350.(2010).
Jiang et al., "Cullin-4A DNA Damage-binding Protein 1 E3 Ligase Complex Targets Tumor Suppressor RASSF1A for Degradation during Mitosis*", *The Journal of Biological Chemistry*, 286(9): 6971-6978 (2011).
Jin et al., "A Family of Diverse Cul4-Ddb1-Interacting Proteins Includes Cdt2, which is Required for S Phase Destruction of the Replication Factor Cdt1", *Molecular Cell*, 23: 709-721 (2006).
Katiyar et al., "REDD1, an inhibitor of mTOR signalling, is regulated by the CUL4A-DDB1 ubiquitin ligase", *EMBO Reports*, 10(8): 866-872 (2009).
Kaur et al.," CRL4-DDB1-VPRBP ubiquitin ligase mediates the stress triggered proteolysis of Mcm10", *Nucleic Acids Research*, 40(15):7332-46 (2012).
Kerzendorfer et al., "Mutations in Cullin 4B result in a human syndrome associated with increased camptothecin-induced topoisomerase I-dependent DNA breaks", *Human Molecular Genetics*, 19(7): 1324-1334 (2010).
Kim et al., "The CRL4 Cdt2 ubiquitin ligase targets the degradation of p21 Cip1 to control replication licensing", *Genes & Development*, 22, 2507-2519 (2008).
Kretz-Remy et al., "Inhibition of IκB-α Phosphorylation and Degradation and Subsequent Nf-κB Activation by Glutathione Peroxidase Overexpression", *The Journal of Cell Biology*, 133(5):1083-1093(1996).

Lee et al., "DCAFs, the Missing Link of the CUL4-DDB1 Ubiquitin Ligase", *Molecular Cell*, 26: 775-780 (2007).
Lee et al., "EZH2 Generates a Methyl Degron that is Recognized by the DCAF1/DDB1/CUL4E3 Ubiquitin Ligase Complex", *Molecular Cell*, 48(4): 572-586 (2012).
Lee et al., "Improved ex vivo expansion of adult hematopoietic stem cells by overcoming CUL4-mediated degradation of HOXB4", *Blood*, 121(20): 4082-4089 (2013).
Li et al., "Structure of DDB1 in Complex with a Paramyxovirus V Protein: Viral Hijack of a Propeller Cluster in Ubiquitin Ligase", *Cell*, 124: 105-117 (2006).
Liu et al., "CUL4A Abrogation Augments DNA Damage Response and Protection against Skin Carcinogenesis", *Molecular Cell*, 34: 451-460 (2009).
Melchor et al.,"Comprehensive characterization of the DNA amplification at 13q34 in human breast cancer reveals TFDP1 and CUL4A as likely candidate target genes", *Breast Cancer Research*, 11(6): 1-14 (2009).
Michiels et al., "Genetic Alterations in Childhood Medulloblastoma Analyzed by Comparative Genomic Hybridization", *Journal of Pediatric Hematology/Oncology*, 24(3): 205-210 (2002).
Nag et al., "The Xeroderma Pigmentosum Group E Gene Product DDB2 is a Specific Target of Cullin 4A in Mammalian Cells", *Molecular and Cellular Biology*, 21(20): 6738-6747 (2001).
Nishitani et al., "CDK Inhibitor p21 is Degraded by a Proliferating Cell Nuclear Antigen-coupled Cul4-DDB1 Cdt2 Pathway during S Phase and after UV Irradiation", *Journal of Biological Chemistry*, 283(43): 29045-29052 (2008).
Oda et al., "Regulation of the Histone H4 Monomethylase PR-Set7 by CRL4Cdt2-Mediated PCNA-Dependent Degradation during DNA Damage", *Molecular Cell*, 40(3): 364-376 (2010).
Ohtake et al., "Dioxin receptor is a ligand-dependent E3 ubiquitin ligase", *Nature* 446: 562-566 (2007).
Petroski et al., "Function and regulation of cullin-RING ubiquitin ligases", *Nature Reviews-Molecular Cell Biology*, 6, 9-20 (2005).
Shinomiya et al.,"Comparative Genomic Hybridization of Squamous Cell Carcinoma of the Esophagus: The Possible Involvement of the DP1 Gene in the 13q34 Amplicon", *Genes, Chromosomes & Cancer*, 24: 337-344 (1999).
Wood et al., "Human DNA Repair Genes", *Science*, 291: 1284-1289 (2001).
Wu et al., "Targeted Ubiquitination and Degradation of G-Protein-Coupled Receptor Kinase 5 by the DDB1-CUL4 Ubiquitin Ligase Complex", *PLoS One*, 7(8): 1-11 (2012).
Yasui et al., "TFDP1, CUL4A, and CDC16 Identified as Targets for Amplification at 13q34 in Hepatocellular Carcinomas", *Hepatology*, 35(6): 1476-1484 (2002).
Zhang et al., "CUL-4A stimulates ubiquitylation and degradation of the HOXA9 homeodomain", *EMBO Journal*, 22(22): 6057-6067 (2003).
Zhang et al., "ETS-1-mediated Transcriptional Up-regulation of CD44 is Required for Sphingosine-1-phosphate Receptor Subtype 3-stimulated Chemotaxis", *The Journal of Biological Chemistry*, 288(45): 32126-32137 (2013).
Lee et al., "Pathogenic role of the CRL4 ubiquitin ligase in human disease", *Frontiers in Oncology*, (2012).
Ren et al., Oncogenic CUL4A determines the response to thalidomide treatment in prostate cancer, *J. Mol Med.*, 90:1121-1132 (2012).
European Patent Office, Extended European Search Report in Application No. 13830939.8 dated Sep. 5, 2016, 10 pages.
European Patent Office, Extended European Search Report in Application No. 13830939.8 dated Feb. 17, 2017, 15 pages.
World Intellectual Property Office, PCT International Search Report in International Application No. PCT/US13/56009 dated Jan. 22, 2014, 3 pages.
Chembridge, "Screening Compounds," ChemBridge Corporation, www.chembridge.com, 1 page (Jan. 19, 2017).

* cited by examiner

Figure 7

| Compound Designation | Compound Chemical Name | Primary Screen: Normalized Percent Inhibition (%) (15µM CpD) | Screen Data - Binding Assay | Confirmation of Binding Assay | In Vitro E3 Inhibition Assay | Compound Structure | Commercially Available? |
|---|---|---|---|---|---|---|---|
| PZ-101 | (5-chloro-2-oxo-2H-1,3-benzoxathiol-6-yl) methyl carbonate | 75.09% | | $IC_{50}=0.236 \mu M$ | ++ | 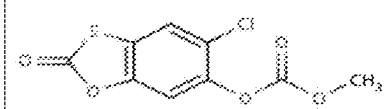 | Yes |
| PZ-102 | (4,6-dibromo-7-methyl-2-oxo-2H-1,3-benzoxathiol-5-yl) methyl carbonate | 94.36% | | $IC_{50}=0.24 \mu M$ | N/A | 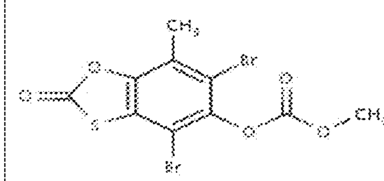 | |
| PZ-103 | (5-bromo-2-oxo-2H-1,3-benzoxathiol-6-yl) ethyl carbonate | 75.70% | | $IC_{50}=2.15 \mu M$ | + | 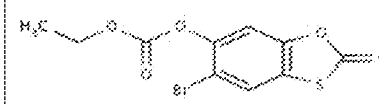 | Yes |

Figure 7 (continued)

| Compound Designation | Compound Chemical Name | Primary Screen: Normalized Percent Inhibition (%) (15µM CpD) | Screen Data - Binding Assay | Confirmation of Binding Assay | In Vitro E3 Inhibition Assay | Compound Structure | Commercially Available? |
|---|---|---|---|---|---|---|---|
| PZ-104 | (5-chloro-2-oxo-2H-1,3-benzoxathiol-6-yl) ethyl carbonate | 76.70% | | $IC_{50}=0.191$ µM | - | 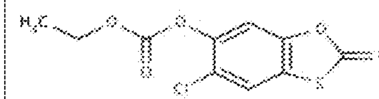 | Yes |
| PZ-105 | 5,7-dibromo-2-oxo-2H-1,3-benzoxathiol-6-yl N-methylcarbamate | 95.97% | | $IC_{50}<0.24$ µM | N/A | 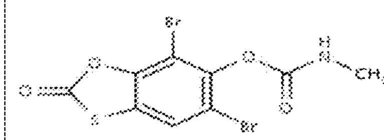 | Yes |
| PZ-106 | (4,6-dichloro-2-oxo-2H-1,3-benzoxathiol-5-yl) ethyl carbonate | 92.87% | | $IC_{50}=0.14$ µM | + | 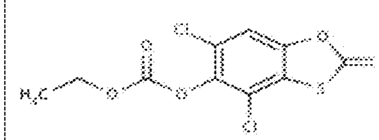 | Yes |

Figure 7 (continued)

| Compound Designation | Compound Chemical Name | Primary Screen: Normalized Percent Inhibition (%) (15μM CpD) | Screen Data – Binding Assay | Confirmation of Binding Assay | In Vitro E3 Inhibition Assay | Compound Structure | Commercially Available? |
|---|---|---|---|---|---|---|---|
| PZ-107 | (5-bromo-2-oxo-2H-1,3-benzoxathiol-6-yl) methyl carbonate | 75.06 |  | $IC_{50}$=1.09 μM | N/A | 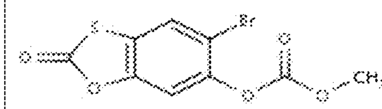 | Yes |
| PZ-108 | 5,7-dibromo-6-hydroxy-2H-1,3-benzoxathiol-2-one | 76.47% | N/A | N/A | + | 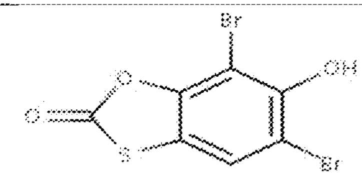 | Yes |
| PZ-109 | | 73.80% | N/A | N/A | N/A | 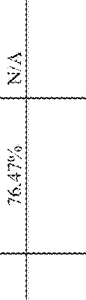 | Yes |

Figure 8

| Compound Designation | Compound Chemical Name | Primary Screen: Normalized Percent Inhibition (%) (15μM CpD) | Screen Data - Binding Assay | Confirmation of Binding Assay | In Vitro E3 Inhibition Assay | Compound Structure | Commercially Available? |
|---|---|---|---|---|---|---|---|
| PZ-201 | 4-(4-methoxyphenyl)-2-sulfanylidene-1,2,5,6,7,8-hexahydroquinoline-3-carbonitrile | 88.69% | 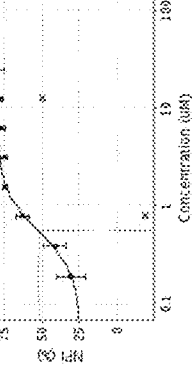 | IC$_{50}$=0.738 μM | ++ | 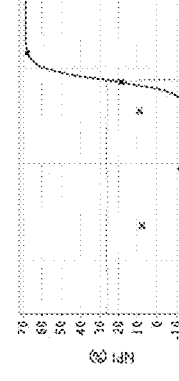 | Yes |
| PZ-202 | 4-(furan-2-yl)-2-sulfanylidene-1,2,5,6,7,8-hexahydroquinoline-3-carbonitrile | 90.02% | 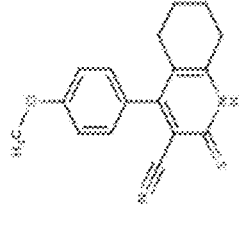 | IC$_{50}$=0.554 μM | ++ | 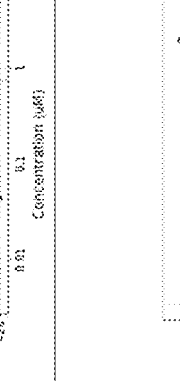 | Yes |

Figure 8 (continued)

| Compound Designation | Compound Chemical Name | Primary Screen: Normalized Percent Inhibition (%) (15μM CpD) | Screen Data – Binding Assay | Confirmation of Binding Assay | In Vitro E3 Inhibition Assay | Compound Structure | Commercially Available? |
|---|---|---|---|---|---|---|---|
| PZ-203 | 4-(4-methoxyphenyl)-2-sulfanylidene-1H,2H,5H,6H,7H-cyclopenta[b]pyridine-3-carbonitrile | 87.73% | | $IC_{50}=0.997$ μM | ++ | 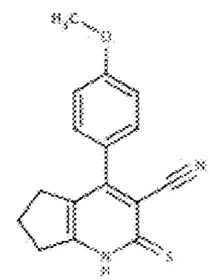 | Yes |
| PZ-204 | 6-cyclopropyl-4-(furan-2-yl)-2-sulfanylidene-1,2-dihydropyridine-3-carbonitrile | 91.43% | | $IC_{50}=4.83$ μM | N/A | 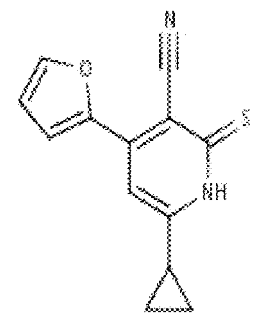 | Yes |

Figure 8 (continued)

| Compound Designation | Compound Chemical Name | Primary Screen: Normalized Percent Inhibition (%) (15μM Cpd) | Screen Data – Binding Assay | Confirmation of Binding Assay | In Vitro E3 Inhibition Assay | Compound Structure | Commercially Available? |
|---|---|---|---|---|---|---|---|
| PZ-205 | 4-(2-fluorophenyl)-2-thioxo-1,2,5,6,7,8-hexahydroquinoline-3-carbonitrile | 75.06 | | $IC_{50}$=2.541 μM | N/A | 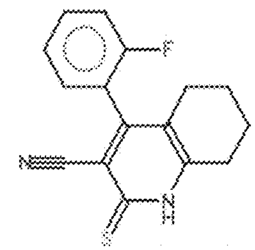 | No |
| PZ-206 | 4-(2-fluorophenyl)-2-thioxo-1,2,5,6,7,8-hexahydroquinoline-3-carbonitrile | 76.47% | | $IC_{50}$=2.68 μM | N/A | 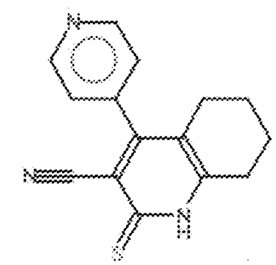 | Yes |
| PZ-207 | 4-(4-methoxyphenyl)-2-thioxo-1,2,5,6,7,8-hexahydroquinoline-3-carbonitrile | 73.80% | | $IC_{50}$=15.8 μM | N/A | 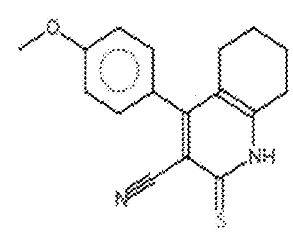 | Yes |

Figure 8 (continued)

| Compound Designation | Compound Chemical Name | Primary Screen: Normalized Percent Inhibition (%) (15µM CpD) | Screen Data - Binding Assay | Confirmation of Binding Assay | In Vitro E3 Inhibition Assay | Compound Structure | Commercially Available? |
|---|---|---|---|---|---|---|---|
| PZ-208 | 4-(furan-2-yl)-2-thioxo-1,2,5,6,7,8-hexahydroquinoline-3-carbonitrile | | 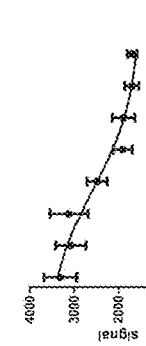 | n/a | N/A | 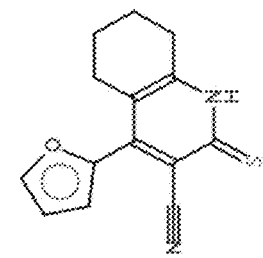 | Yes |
| PZ-209 | 4-(4-hydroxyphenyl)-2-thioxo-1,2,5,6,7,8-hexahydroquinoline-3-carbonitrile | | 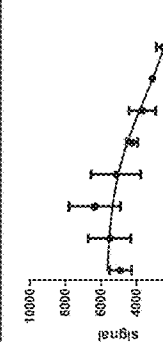 | IC$_{50}$=0.114 µM | N/A | 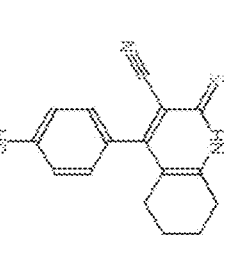 | Yes |

Figure 9

| Compound Designation | Compound Chemical Name | Primary Screen: Normalized Percent Inhibition (%) (15μM CpD) | Screen Data - Binding Assay | Confirmation of Binding Assay | In Vitro E3 Inhibition Assay | Compound Structure | Commercially Available? |
|---|---|---|---|---|---|---|---|
| PZ-301 | 2,6-diamino-4-(furan-2-yl)-4H-thiopyran-3,5-dicarbonitrile | 82.92% | 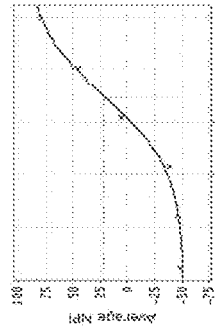 | IC$_{50}$=1.6 mM | ++ | 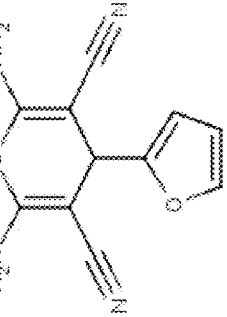 | Yes |
| PZ-302 | 2,6-diamino-4-(5-bromo-2-fluorophenyl)-4H-thiopyran-3,5-dicarbonitrile | 67.73% | 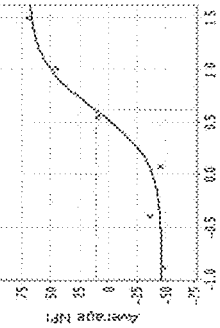 | IC$_{50}$=0.69 mM | N/A | 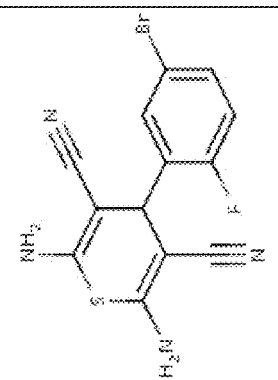 | Yes |

Figure 9 (continued)

| Compound Designation | Compound Chemical Name | Primary Screen: Normalized Percent Inhibition (%) (15µM CpD) | Screen Data - Binding Assay | Confirmation of Binding Assay | In Vitro E3 Inhibition Assay | Compound Structure | Commercially Available? |
|---|---|---|---|---|---|---|---|
| PZ-303 | 2,6-diamino-4-(thiophen-2-yl)-4H-thiopyran-3,5-dicarbonitrile | 78.91% | 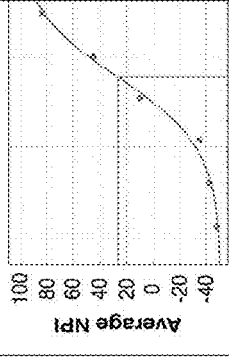 | $IC_{50}$=1.46 mM | +++ | 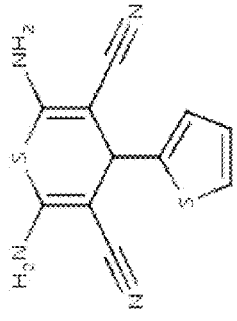 | Yes |
| PZ-304 | 2,6-diamino-4-(quinolin-4-yl)-4H-thiopyran-3,5-dicarbonitrile | 67.22% | 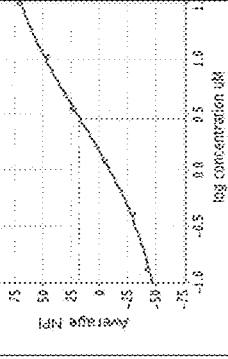 | $IC_{50}$=2.91 mM | N/A | 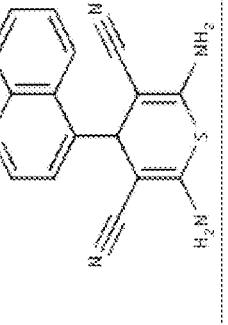 | Yes |
| PZ-305 | 2,6-diamino-4-(2-fluorophenyl)-4H-thiopyran-3,5-dicarbonitrile | 79.64% | ND | ND | ++ | 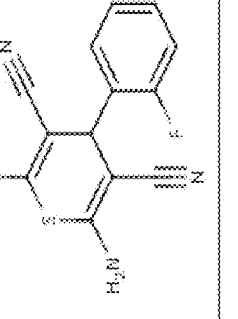 | Yes |

Figure 9 (continued)

| Compound Designation | Compound Chemical Name | Primary Screen: Normalized Percent Inhibition (%) (15μM CpD) | Screen Data - Binding Assay | Confirmation of Binding Assay | In Vitro E3 Inhibition Assay | Compound Structure | Commercially Available? |
|---|---|---|---|---|---|---|---|
| PZ-306 | 2,6-diamino-4-phenyl-4H-thiopyran-3,5-dicarbonitrile | N/A | | $IC_{50}$=5.04 μM | N/A | 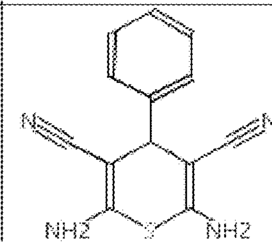 | Yes |
| PZ-307 | 2,6-diamino-4-phenethyl-4H-thiopyran-3,5-dicarbonitrile | N/A | | $IC_{50}$=3.68 μM | N/A | 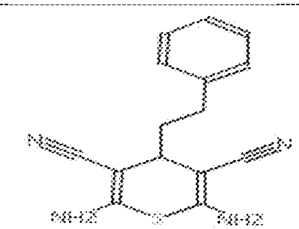 | Yes |
| PZ-308 | 2,6-diamino-4-(2-nitrophenyl)-4H-thiopyran-3,5-dicarbonitrile | N/A | | $IC_{50}$=8.492 μM | N/A | 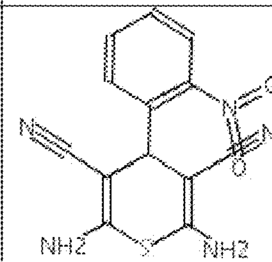 | Yes |

Figure 9 (continued)

| Compound Designation | Compound Chemical Name | Primary Screen: Normalized Percent Inhibition (%) (15µM CpD) | Screen Data – Binding Assay | Confirmation of Binding Assay | In Vitro E3 Inhibition Assay | Compound Structure | Commercially Available? |
|---|---|---|---|---|---|---|---|
| PZ-309 | 2,6-diamino-4-(4-(trifluoromethyl)phenyl)-4H-thiopyran-3,5-dicarbonitrile | N/A | (binding curve) | $IC_{50} > 50$ uM | N/A | (structure) | Yes |
| PZ-310 | 2,6-diamino-4-(2,6-difluorophenyl)-4H-thiopyran-3,5-dicarbonitrile | N/A | (binding curve) | $IC_{50} = 15.29$ nM | N/A | (structure) | Yes |
| PZ-311 | 2,6-diamino-4-(3-fluorophenyl)-4H-thiopyran-3,5-dicarbonitrile | N/A | ND | N/A | N/A | (structure) | Yes |

Figure 9 (continued)

| Compound Designation | Compound Chemical Name | Primary Screen: Normalized Percent Inhibition (%) (15μM CpD) | Screen Data - Binding Assay | Confirmation of Binding Assay | In Vitro E3 Inhibition Assay | Compound Structure | Commercially Available? |
|---|---|---|---|---|---|---|---|
| PZ-312 | 2,6-diamino-4-(2-(trifluoromethyl)phenyl)-4H-thiopyran-3,5-dicarbonitrile | N/A | [graph] | $IC_{50}$=1.856 μM | N/A | [structure] | Yes |
| PZ-313 | 2,6-diamino-4-(pyridin-4-yl)-4H-thiopyran-3,5-dicarbonitrile | N/A | [graph] | $IC_{50}$=2.599 μM | N/A | [structure] | Yes |
| PZ-314 | 2,6-diamino-4-(4-chlorophenyl)-4H-thiopyran-3,5-dicarbonitrile | N/A | ND | N/A | N/A | [structure] | Yes |

Figure 9 (continued)

| Compound Designation | Compound Chemical Name | Primary Screen: Normalized Percent Inhibition (%) (15µM CpD) | Screen Data - Binding Assay | Confirmation of Binding Assay | In Vitro E3 Inhibition Assay | Compound Structure | Commercially Available? |
|---|---|---|---|---|---|---|---|
| PZ-315 | 2,6-diamino-4-(4-methoxyphenyl)-4H-thiopyran-3,5-dicarbonitrile | N/A | ND | N/A | N/A | 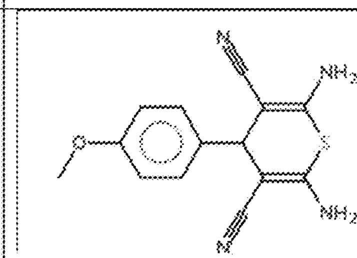 | Yes |
| PZ-316 | 2,6-diamino-4-(furan-2-yl)-4H-thiopyran-3,5-dicarbonitrile | N/A | ND | N/A | N/A | 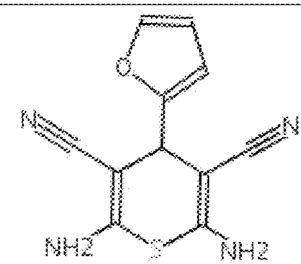 | Yes |
| PZ-317 | 4-(2,6-diamino-3,5-dicyano-4H-thiopyran-4-yl)phenyl acetate | N/A | [graph] | $IC_{50} = 41.25\ \mu M$ | N/A | 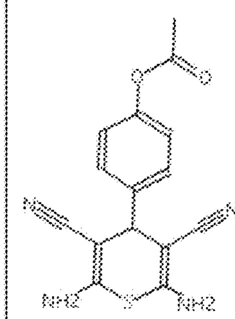 | Yes |

Figure 9 (continued)

| Compound Designation | Compound Chemical Name | Primary Screen: Normalized Percent Inhibition (%) (15µM CpD) | Screen Data – Binding Assay | Confirmation of Binding Assay | In Vitro E3 Inhibition Assay | Compound Structure | Commercially Available? |
|---|---|---|---|---|---|---|---|
| PZ-318 | 2,6-diamino-4-(4-fluorophenyl)-4H-thiopyran-3,5-dicarbonitrile | N/A | 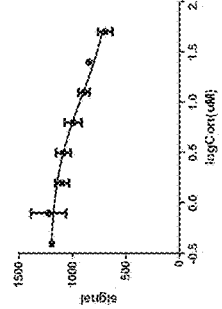 | IC$_{50}$=11.34 µM | N/A | 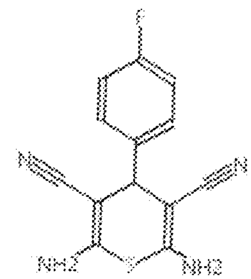 | Yes |
| PZ-319 | 6-diamino-4-(4-chlorophenyl)-2-mercapto-5-(piperidine-1carbonyl)nicotinonitrile | N/A | 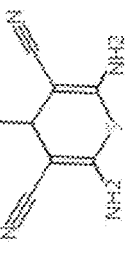 | IC$_{50}$=52.53 µM | N/A | 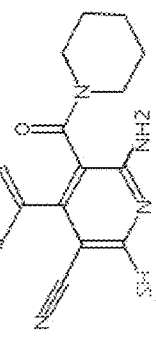 | No |

Figure 10

| Compound Designation | Compound Chemical Name | Primary Screen: Normalized Percent Inhibition (%) (15μM CpD) | Screen Data – Binding Assay | Confirmation of Binding Assay | In Vitro E3 Inhibition Assay | Compound Structure | Commercially Available? |
|---|---|---|---|---|---|---|---|
| PZ-401 | 5-(4-methoxyphenyl)-4-(4-methylphenyl)-4H-1,2,4-triazole-3-thiol | 77.90% | | IC$_{50}$=2.4 μM | + | 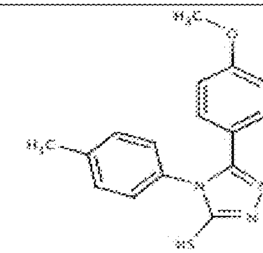 | Yes |
| PZ-402 | 4-(3,4-dichlorophenyl)-5-(propan-2-yl)-4H-1,2,4-triazole-3-thiol | 69.69% | | IC$_{50}$<0.24 μM | + | 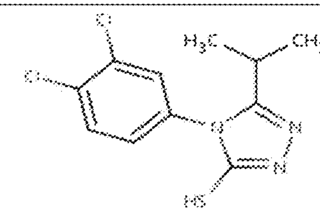 | Yes |

Figure 10 (continued)

| Compound Designation | Compound Chemical Name | Primary Screen: Normalized Percent Inhibition (%) (15μM CpD) | Screen Data – Binding Assay | Confirmation of Binding Assay | In Vitro E3 Inhibition Assay | Compound Structure | Commercially Available? |
|---|---|---|---|---|---|---|---|
| PZ-403 | 5-cyclopropyl-4-(3,4-dichlorophenyl)-4H-1,2,4-triazole-3-thiol | 70.12% | | IC50=0.703 mM | +++ | 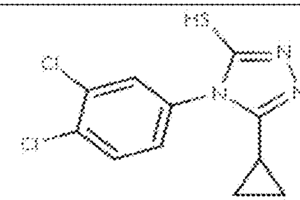 | Yes |

Figure 11

| Compound Designation | Compound Chemical Name | Primary Screen: Normalized Percent Inhibition (%) (15uM CpD) | Screen Data – Binding Assay | Confirmation of Binding Assay | In Vitro E3 Inhibition Assay | Compound Structure | Commercially Available? |
|---|---|---|---|---|---|---|---|
| PZ-501 | 5-bromo-1-(2-oxopropyl)-2,3-dihydro-1H-indole-2,3-dione | 87.92% | 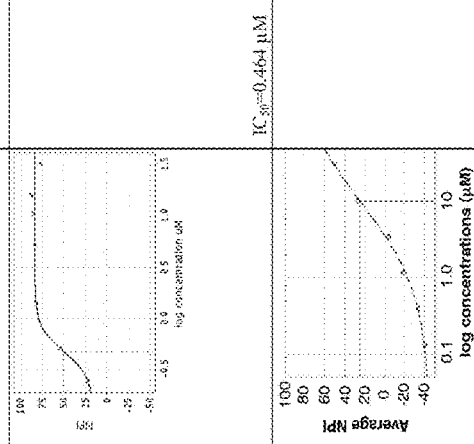 | IC$_{50}$=0.464 µM | ++ | 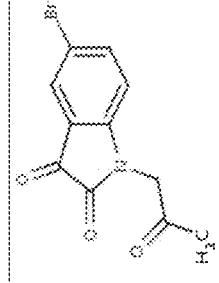 | Yes |
| PZ-601 | 3,3-dimethyl-8-(piperazin-1-yl)-6-sulfanylidene-1H,3H,4H,6H,7H-pyrano[3,4-c]pyridine-5-carbonitrile | 78.31% | 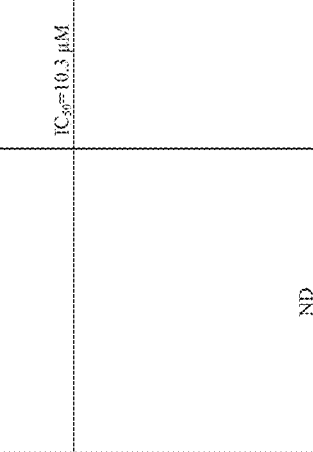 | IC$_{50}$=10.3 µM | ++ | 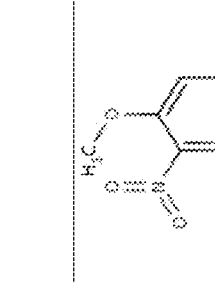 | Yes |
| PZ-701 | 3-bromo-5-methoxy-2,6-dinitropyridine | 70.74% | ND | N/A | ++ | 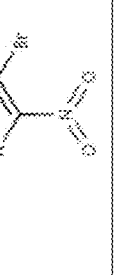 | Yes |

Figure 11 (continued)

| Compound Designation | Compound Chemical Name | Primary Screen: Normalized Percent Inhibition (%) (15μM CpD) | Screen Data – Binding Assay | Confirmation of Binding Assay | In Vitro E3 Inhibition Assay | Compound Structure | Commercially Available? |
|---|---|---|---|---|---|---|---|
| PZ-801 | 10-thia-3,5,6,8-tetraazatetracyclo[7.7.0.0^{2,6}.0^{11,16}]hexadeca-1(9),2,4,11(16)-tetraen-7-one | 78.71% | | IC$_{50}$=1.05 μM | ++ | 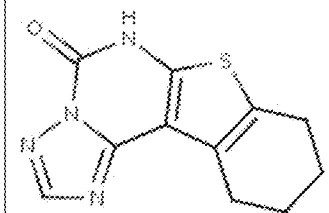 | Yes |
| PZ-901 | 5-iodo-3-methoxy-1,2-thiazole-4-carbonitrile | 84.72% | | IC$_{50}$=4.39 mM | ++ | 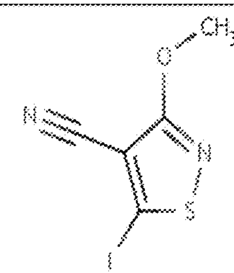 | Yes |
| PZ-1001 | [1-(6-chloro-5-nitropyrimidin-4-yl)piperidin-2-yl]methanol | 90.44% | | IC$_{50}$=4.61 μM | – | 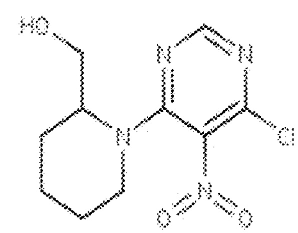 | Yes |

Figure 11 (continued)

| Compound Designation | Compound Chemical Name | Primary Screen: Normalized Percent Inhibition (%) (15μM CpD) | Screen Data – Binding Assay | Confirmation of Binding Assay | In Vitro E3 Inhibition Assay | Compound Structure | Commercially Available? |
|---|---|---|---|---|---|---|---|
| PZ-1101 | 4,8-dichloro-[1,2,3,4]tetrazolo[1,5-a]quinoxaline | 98.84% | 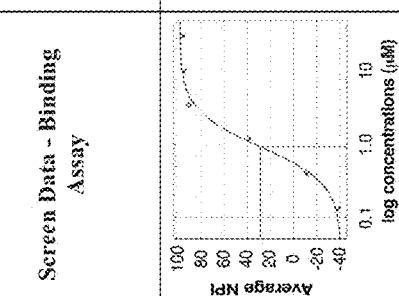 | $IC_{50}=0.943$ μM | ++ | 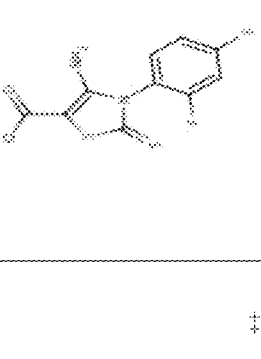 | Yes |
| PZ-1201 | methyl 4-amino-3-(2,4-difluorophenyl)-2-sulfanylidene-2,3-dihydro-1,3-thiazole-5-carboxylate | 93.19% | N/A | N/A | ++ | 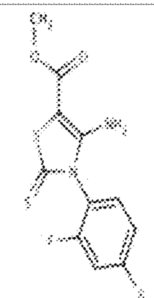 | Yes |

INHIBITORS OF CRL4 UBIQUITIN LIGASE AND USES THEREOF

CROSS-REFERENCE TO RELATED APPLICATIONS

This patent application claims the benefit of U.S. Provisional Patent Application No. 61/691,539 filed Aug. 21, 2012, which is incorporated by reference.

BACKGROUND OF THE INVENTION

Cells are continually exposed to factors, such as intracellular reactive species and environmental agents, which are capable of causing DNA damage. The potentially mutagenic consequences of DNA damage are minimized by DNA repair pathways, which are broadly characterized into three forms: base excision repair (BER), mismatch repair (MMR), and nucleotide excision repair (NER) (Wood et al., Science, 291: 1284-1289 (2001)). Deficiencies in DNA damage repair underlie the pathogenesis of cancer as well as many genetic disorders.

The gene encoding the CUL4A ubiquitin ligase (also referred to in the art as Cullin Ring Ligase 4 (CRL4) and Cullin-4A) is frequently amplified or overexpressed in a wide variety of cancer types, such as breast cancer (Chen et al., Cancer Res., 58: 3677-3683 (1998); and Melchor et al., Breast Cancer Res., 11: R86 (2009)), hepatocellular carcinoma (Yasui et al., Hepatology, 35: 1476-1484 (2002)), colon cancer, squamous cell carcinoma (Shinomiya et al., Genes Chromosomes Cancer, 24: 337-344 (1999)), adrenocortical carcinoma (Dohna et al., Genes Chromosomes Cancer, 28: 145-152 (2000)), childhood medulloblastoma (Michiels et al., J. Pediatr. Hematol. Oncol., 24: 205-210 (2002)), and primary malignant pleural mesothelioma (Hung et al., J. Cell. Mol. Med., 15(2): 350-358 (2011)).

CUL4A functions as a component of a multimeric protein complex wherein the C-terminus of CUL4A interacts with the RING finger protein Rbx1/ROC1/Hrt1 (hereinafter referred to as Rbx1) to recruit the E2 ubiquitin-conjugating enzyme, and the N-terminus of CUL4A interacts with damage-specific DNA binding protein 1 (DDB1). DDB1, in turn, acts as an adaptor, binding to DDB1, CUL4A associated factors (DCAFs), which serve as specific substrate receptors (Angers et al., Nature, 443: 590-593 (2006); He et al., Genes Dev., 20: 2949-2954 (2006); Higa et al., Nat Cell Biol., 8: 1277-1283 (2006); Jin et al., Mol. Cell, 23: 709-721 (2006); Lee and Zhou, Mol. Cell, 26: 775-780 (2007)).

While the components of the multimeric CUL4A ubiquitination complex and several cellular targets (e.g. Cdt1, c-Jun, HOXA9, DDB2, XPC, p21, E2F1, REDD1) (reviewed in Lee and Zhou, Mol. Cell., 26: 775-780 (2007)) have been identified, the physiological role of CUL4A in tumorigenesis remains largely unknown. Damage-specific DNA binding protein 2 (DDB2) has been shown to be subjected to CUL4A-dependent ubiquitination and degradation, which leads to an overall decrease in the ability to recognize DNA lesions (Chen et al., J. Biol. Chem., 276: 48175-48182 (2001); and Nag et al., Mol. Cell Biol., 21(20): 6738-47 (2001)). Other studies have shown that the cyclin-dependent kinase inhibitor p21 is also a substrate of the CUL4A ubiquitin ligase (Abbas et al., Genes Dev., 22: 2496-2506 (2008)); Cang et al., Cell, 127: 929-940 (2006); and Kim et al., Genes Dev., 22, 2507-2519 (2008)). Conditional CUL4A knockout mice exhibit increased accumulation of DDB2 and p21, resulting in both enhanced repair activity in the removal of strand-distorting DNA lesions induced by UV (e.g. cyclobutane pyrimidine dimers (CPDs) and 6,4-photoproducts (6,4-PPs)), and prolonged G1/S DNA damage checkpoint that allows additional time for the NER machinery to remove the DNA lesions (Liu et al., Mol. Cell., 34: 451-460 (2009) and U.S. Pat. No. 8,513,181). In addition, skin-specific deletion of CUL4A rendered the knockout mice resistant to UV-induced skin carcinogenesis (Liu et al., Mol. Cell., 34: 451-460 (2009)). As such, inhibiting CUL4A may be a potential therapeutic strategy for both prevention and treatment of human cancers.

There is a need for compositions and methods to inhibit CUL4A activity for the treatment of cancer. This invention provides such compositions and methods.

BRIEF SUMMARY OF THE INVENTION

The invention provides a method of treating a cancer in an animal. The method comprises administering to an animal in need thereof an effective amount of a substance that interferes with the activity of CUL4A, wherein the substance is a 1,3-benzoxathiol-2-one compound, a pyridine thione compound, a 2,6-diamino-4-thiopyran-3,5-dicarbonitrile compound, a 1,2,4-triazole-3-thiol compound, 5-bromo-1-(2-oxopropyl)-2,3-dihydro-1H-indole-2,3-dione; 3,3-dimethyl-8-(piperazin-1-yl)-6-sulfanylidene-1H,3H,4H,6H,7H-pyrano[3,4-c]pyridine-5-carbonitrile; 3-bromo-5-methoxy-2,6-dinitropyridine; 10-thia-3,5,6,8-tetraazatetracyclo[7.7.0.0^{2,6}.0^{11,16}]hexadeca-1(9),2,4,11(16)-tetraen-7-one; 5-iodo-3-methoxy-1,2-thiazole-4-carbonitrile; [1-(6-chloro-5-nitropyrimidin-4-yl)piperidin-2-yl]methanol; 4,8-dichloro-[1,2,3,4]tetrazolo[1,5-a]quinoxaline; or methyl 4-amino-3-(2,4-difluorophenyl)-2-sulfanylidene-2,3-dihydro-1,3-thiazole-5-carboxylate, thereby treating a cancer in the animal.

The invention also provides a method of increasing DNA repair activity in an animal. The method comprises administering to an animal in need thereof an effective amount of a substance that interferes with the activity of CUL4A, wherein the substance is a 1,3-benzoxathiol-2-one compound; a pyridine thione compound; a 2,6-diamino-4-thiopyran-3,5-dicarbonitrile compound; a 1,2,4-triazole-3-thiol compound; 5-bromo-1-(2-oxopropyl)-2,3-dihydro-1H-indole-2,3-dione; 3,3-dimethyl-8-(piperazin-1-yl)-6-sulfanylidene-1H,3H,4H,6H,7H-pyrano[3,4-c]pyridine-5-carbonitrile; 3-bromo-5-methoxy-2,6-dinitropyridine; 10-thia-3,5,6,8-tetraazatetracyclo[7.7.0.0^{2,6}.0^{11,16}]hexadeca-1(9),2,4,11(16)-tetraen-7-one, 5-iodo-3-methoxy-1,2-thiazole-4-carbonitrile; [1-(6-chloro-5-nitropyrimidin-4-yl)piperidin-2-yl]methanol; 4,8-dichloro-[1,2,3,4]tetrazolo[1,5-a]quinoxaline; or methyl 4-amino-3-(2,4-difluorophenyl)-2-sulfanylidene-2,3-dihydro-1,3-thiazole-5-carboxylate, thereby increasing DNA repair activity in the animal.

BRIEF DESCRIPTION OF THE SEVERAL VIEWS OF THE DRAWING(S)

FIG. 1 is an image which depicts experimental data illustrating inhibition of CUL4A ubiquitin ligase activity by small molecules compounds (or "hit compounds") identified in Example 1. 50 µM of individual compounds were tested in an in vitro DDB1 ubiquitination reaction that contains affinity-purified recombinant proteins as indicated. The tested compounds, which are described in detail in FIGS. 7-11, included the following small molecule compounds: PZ-104 (lane 1); PZ-108 (lane 2); PZ-106 (lane 3); PZ-101 (lane 4); PZ-103 (lane 5); PZ-501 (lane 6); PZ-202 (lane 7); PZ-203 (lane 8); PZ-201 (lane 9); PZ-301 (lane 10); PZ-305

(lane 11); PZ-303 (lane 12); PZ-601 (lane 13); PZ-701 (lane 14); PZ-701 (lane 15); PZ-901 (lane 16); PZ-1001 (lane 17); PZ-1101 (lane 18); PZ-1201 (lane 19); PZ-401 (lane Ni); PZ-402 (lane IV2); and PZ-403 (lane IV3).

FIG. 2 is an image which depicts experimental data illustrating the results of a cell-based DDB2 degradation assay. The tested compounds, which are described in detail in FIGS. 7-11, included the following small molecule compounds: PZ-104 (lane 1); PZ-108 (lane 2); PZ-106 (lane 3); PZ-101 (lane 4); PZ-103 (lane 5); PZ-501 (lane 6); PZ-202 (lane 7); PZ-203 (lane 8); PZ-201 (lane 9); PZ-301 (lane 10); PZ-305 (lane 11); PZ-303 (lane 12); PZ-601 (lane 13); PZ-701 (lane 14); PZ-701 (lane 15); PZ-901 (lane 16); PZ-1001 (lane 17); PZ-1101 (lane 18); PZ-1201 (lane 19); PZ-401 (lane IV1); PZ-402 (lane IV2); and PZ-403 (IV3). MG132, a proteasome inhibitor that blocks UV-induced DDB2 degradation, was a positive control. Tubulin levels were determined by Western blotting as a loading control.

FIG. 3 is an image which depicts experimental data illustrating the results of a cell-based DDB2 degradation assay which tested dose-dependent inhibition of CUL4A ubiquitin ligase by pyridine thione-containing compounds and 2,6-diamino-4-thiopyran-3,5-dicarbonitrile-containing compounds identified in Example 1. The tested compounds, which are described in detail in FIGS. 8 and 9, included the following small molecule compounds: PZ-202; PZ-203; PZ-201; PZ-301; PZ-305; and PZ-303.

FIG. 4 is an image which depicts experimental data illustrating the results of an assay to examine the specificity of the hit compounds for CUL4A described in Example 1. The tested compounds, which are described in detail in FIGS. 8 and 9, included the following small molecule compounds: PZ-202 (#7); PZ-203 (#8); PZ-201 (#9); PZ-301 (#10); PZ-305 (#11); and PZ-303 (#12).

FIG. 5 is an image which depicts experimental data illustrating the results of a cell-based AhR degradation assay. The tested compounds, which are described in detail in FIGS. 7-11, included the following small molecule compounds PZ-202 (lane 4); PZ-203 (lane 5); PZ-201 (lane 6); PZ-301 (lane 7); PZ-305 (lane 8); PZ-303 (lane 9); PZ-401 (lane 10); PZ-402 (lane 11); PZ-403 (lane 12); PZ-108 (lane 13); and PZ-901 (lane 14).

FIG. 7 is a table describing features of select 1,3-benzoxathiol-2-one compounds in accordance with embodiments of the disclosure.

FIG. 8 is a table describing features of select pyridine thione compounds in accordance with embodiments of the disclosure.

FIG. 9 is a table describing features of select 2,6-diamino-4-thiopyran-3,5-dicarbonitrile compounds in accordance with embodiments of the disclosure.

FIG. 10 is a table describing features of select 1,2,4-triazole-3-thiol compounds in accordance with embodiments of the disclosure.

FIG. 11 is a table describing features of compounds with unique chemical structures in accordance with embodiments of the disclosure.

DETAILED DESCRIPTION OF THE INVENTION

Figure 1:
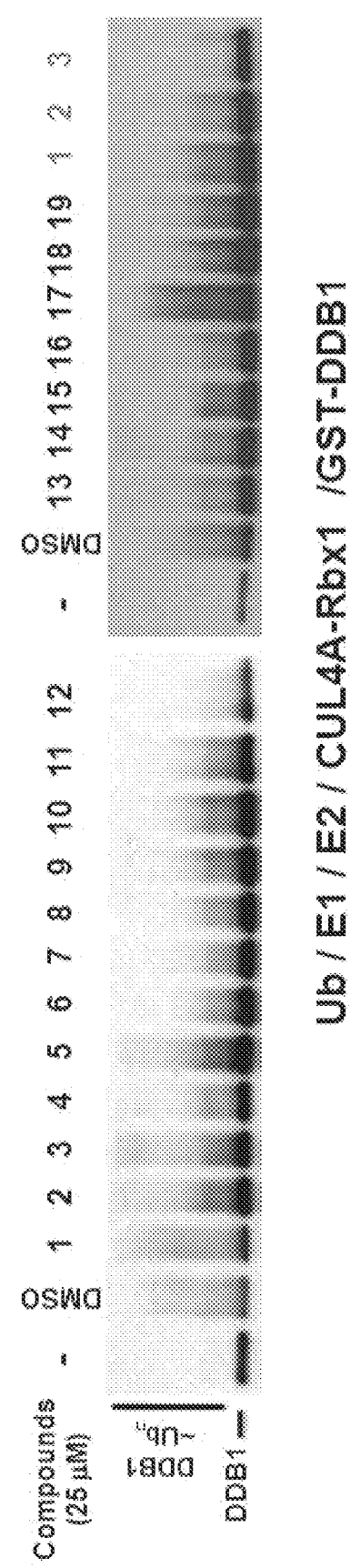

The invention is based, at least in part, upon the discovery that the DDB1-CUL4A ubiquitin ligase complex is an important cellular target for cancer prevention and intervention. In this respect, RNAi-mediated inhibition of CUL4A ubiquitin ligase activity in breast cancer or mesothelioma cells results in either massive apoptosis, or growth arrest (see, e.g., Hung et al., *J. Cell Mol. Med.*, 15(2): 350-358 (2011)). In addition, topoisomerase 1 (TOP1) is a specific target of CUL4 E3 ligase following exposure of cells to camptothecin (CPT)-type drugs (Kerzendorfer et al., *Hum. Mol. Genet.*, 19: 1324-1334 (2010)). Thus, inhibition of CUL4A ubiquitin ligase should enhance the therapeutic efficacy of the topoisomerase 1 (TOP1)-directed anti-cancer drugs, including, for example, CPT, topotecan, and irinotecan. The invention provides a method of preventing or treating a cancer in an animal, which method comprises administering to an animal in need thereof an effective amount of a substance that interferes with the activity of CUL4A, wherein the substance is a 1,3-benzoxathiol-2-one compound, a pyridine thione compound, a 2,6-diamino-4-thiopyran-3,5-dicarbonitrile compound, a 1,2,4-triazole-3-thiol compound, 5-bromo-1-(2-oxopropyl)-2,3-dihydro-1H-indole-2,3-dione; 3,3-dimethyl-8-(piperazin-1-yl)-6-sulfanylidene-1H,3H,4H,6H,7H-pyrano[3,4-c]pyridine-5-carbonitrile; 3-bromo-5-methoxy-2,6-dinitropyridine; 10-thia-3,5,6,8-tetraazatetracyclo[7.7.0.0^{2,6}.0^{11,16}]hexadeca-1(9),2,4,11(16)-tetraen-7-one, 5-iodo-3-methoxy-1,2-thiazole-4-carbonitrile; [1-(6-chloro-5-nitropyrimidin-4-yl)piperidin-2-yl]methanol; 4,8-dichloro-[1,2,3,4]tetrazolo[1,5-a]quinoxaline; or methyl 4-amino-3-(2,4-difluorophenyl)-2-sulfanylidene-2,3-dihydro-1,3-thiazole-5-carboxylate, thereby treating a cancer in the animal.

CUL4A is a ubiquitin ligase which functions as a component of a multimeric protein complex wherein the C-terminus of CUL4A interacts with the RING finger protein Rbx1 to recruit the E2 ubiquitin-conjugating enzyme, and the N-terminus of CUL4A interacts with DDB1. DDB1, in turn, acts as an adaptor, binding to DDB1, CUL4A associated factors (DCAFs), which serve as specific substrate receptors (Angers et al., *Nature*, 443: 590-593 (2006); He et al., *Genes Dev.*, 20: 2949-2954 (2006); Higa et al., *Nat Cell Biol.*, 8: 1277-1283 (2006); Jin et al., *Mol. Cell*, 23: 709-721 (2006); Lee and Zhou, *Mol. Cell*, 26: 775-780 (2007)). Substrates for ubiquitination by CUL4A-containing complexes include c-Jun, DDB2, XPC, p21, PR-Set7/Set8, TSC2, HOXA9, HOXB4, the p12 subunit of DNA polymerase δ, CHK1 kinase, RORα, GRK5, androgen receptor, MCM10, RASSF1A, and REDD1 (see, e.g., Li et al., *Cell*, 124: 105-117 (2006); Nishitani et al., *J. Biol. Chem.*, 283: 29045-52 (2008); Oda et al., *Mol. Cell.*, 40(3): 364-376 (2010); Abbas et al., *Mol. Cell.*, 49(6): 1147-1158 (2013); Centore et al., *Mol. Cell.*, 40(1): 22-33 (2010); Hu et al., *Genes Dev.*, 22(7): 866-871 (2008); Zhang et al., *EMBO J.*, 22(22): 6057-6067 (2003); Lee et al., *Blood*, 121(20): 4082-4089 (2013); Zhang et al., *J. Biol. Chem.*, Aug. 2, 2013 [Epub ahead of print]), Huh et al., *Mol. Cell., Biol.*, 33(2): 213-226 (2013); Lee et al., *Mol. Cell.*, 48(4): 572-86 (2012); Wu et al., *PLoS One*, 7(8): e43997 (Epub 2012); Chang et al., *Int. J. Biochem. Cell. Biol.*, 44(11): 1952-1961 (2012); Kaur et al., *Nucleic Acids Res.*, 40(15):7332-46 (2012); Jiang et al., *J. Biol. Chem.*, 286(9): 6971-6978 (2011); and Katiyar et al., *EMBO Rep.*, 10(8): 866-72 (2009)).

The invention provides a substance that interferes with the activity of CUL4A. As used herein, the terms "substance," "compound," and "therapeutic agent" refer to a chemical compound, a mixture of chemical compounds, a biological macromolecule, or an extract made from biological materials such as bacteria, plants, fungi, or animal (particularly mammalian) cells or tissues that are suspected of having therapeutic properties. The substance, compound, or therapeutic agent can be purified, substantially purified or partially purified. Preferably the substance is a small molecule chemical compound. As used herein, the term "small molecule" refers to a non-biological substance or compound having a molecular weight of less than about 1,000 g/mol.

As used herein, the term "interferes with the activity of CUL4A" refers to the ability of a substance to inhibit the expression and/or biochemical or biological function of CUL4A. Examples of biochemical functions of CUL4A include, without limitation, binding to DDB1, binding to CUL4A, binding to Rbx1, binding to DCAFs, and having ubiquitin ligase activity (e.g., ubiquitinating and destabilizing p21, ubiquitinating and destabilizing DDB2, and ubiquitinating and destabilizing HOXB4). In one embodiment, the substance that interferes with the activity of CUL4A disrupts the binding of CUL4A to damaged DNA binding protein 1 (DDB1). Preferably, the substance disrupts the interaction of the N-terminal α-helical region of CUL4A with the BPB β-propeller domain of DDB1. The substance that disrupts the binding of CUL4A to DDB1 may interact directly with CUL4A and/or DDB1 or act indirectly (or allosterically) by binding to another component of a CUL4A-DDB1 containing complex. In one embodiment, the substance that interferes with the activity of CUL4A competitively inhibits the binding of an endogenous CUL4A to DDB1 in an animal. Examples of biological functions of CUL4A include, without limitation, the regulation of cell proliferation, cell survival, DNA repair, and genomic integrity (Lee and Zhou, Mol. Cell, 26: 775-780 (2007)). In one embodiment, the substance that interferes with the activity of CUL4A causes an increase in DNA repair activity. In another embodiment, the substance that interferes with the activity of CUL4A causes an increase in nucleotide excision repair activity. Thus, the invention also provides a method of increasing DNA repair activity in an animal which comprises administering to an animal in need thereof an effective amount of a substance that interferes with the activity of CUL4A. The substance that interferes with the activity of CUL4A also can interfere with the activity of CUL4B, inasmuch as CUL4A and CUL4B exhibit redundant, isoform-specific activities.

In one embodiment, the substance that interferes with the activity of CUL4A inhibits ubiquitin ligase activity by at least 25% (e.g., 25% or more, 35% or more, or 45% or more) compared to ubiquitin ligase activity in the absence of the interfering substance. Preferably, the substance that interferes with the activity of CUL4A inhibits ubiquitin ligase activity by at least 50% (e.g., 50% or more, 60% or more, or 70% or more) compared to ubiquitin ligase activity in the absence of the interfering substance. Most preferably, the substance that interferes with the activity of CUL4A inhibits ubiquitin ligase activity by at least 75% (e.g., 75% or more, 85% or more, or 95% or more) compared to ubiquitin ligase activity in the absence of the interfering substance. Whether the substance interferes with the expression of CUL4A or a biochemical or biological function of CUL4A, the degree of inhibition may be partially complete (e.g., 10% or more, 25% or more, 50% or more, or 75% or more), substantially complete (e.g., 85% or more, 90% or more, or 95% or more), or fully complete (e.g., 98% or more, or 99% or more).

In one embodiment, the substance that interferes with the activity of CUL4A is a 1,3-benzoxathiol-2-one compound. The term "1,3-benzoxathiol-2-one compound" refers to any compound which comprises at least one 1,3-benzoxathiol-2-one moiety, and can also be referred to as a "1,3-benzoxathiol-2-one-containing compound" or a "1,3-benzoxa-thiol-2-one-based" compound. Any suitable 1,3-benzoxathiol-2-one compound can be used in the inventive method. Suitable 1,3-benzoxathiol-2-one compounds are known in the art, are commercially available, and include, for example, (5-chloro-2-oxo-2H-1,3-benzoxathiol-6-yl) methyl carbonate; (4,6-dibromo-7-methyl-2-oxo-2H-1,3-benzoxathiol-5-yl) methyl carbonate; (5-bromo-2-oxo-2H-1,3-benzoxathiol-6-yl) ethyl carbonate; (5-chloro-2-oxo-2H-1,3-benzoxathiol-6-yl) ethyl carbonate; 5,7-dibromo-2-oxo-2H-1,3-benzoxathiol-6-yl N-methylcarbamate; (4,6-dichloro-2-oxo-2H-1,3-benzoxathiol-5-yl) ethyl carbonate; (5-bromo-2-oxo-2H-1,3-benzoxathiol-6-yl) methyl carbonate; and 5,7-dibromo-6-hydroxy-2H-1,3-benzoxathiol-2-one. The structures of the aforementioned 1,3-benzoxathiol-2-one compounds are set forth in Table 1.

In another embodiment, the substance that interferes with the activity of CUL4A is a pyridine thione compound. The term "pyridine thione" refers to any compound which comprises at least one pyridine thione moiety, and can also be referred to as a "pyridine thione-containing compound" or a "pyridine-thione-based" compound. Any suitable pyridine thione compound can be used in the inventive method. Suitable pyridine thione compounds are known in the art, are commercially available, and include, for example, 4-(4-methoxyphenyl)-2-sulfanylidene-1,2,5,6,7,8-hexahydroquinoline-3-carbonitrile; 4-(furan-2-yl)-2-sulfanylidene-1,2,5,6,7,8-hexahydroquinoline-3-carbonitrile; 4-(4-methoxyphenyl)-2-sulfanylidene-1H,2H,5H,6H,7H-cyclopenta[b]pyridine-3-carbonitrile; 6-cyclopropyl-4-(furan-2-yl)-2-sulfanylidene-1,2-dihydropyridine-3-carbonitrile; 4-(2-fluorophenyl)-2-thioxo-1,2,5,6,7,8-hexahydroquinoline-3-carbonitrile; 4-(2-fluorophenyl)-2-thioxo-1,2,5,6,7,8-hexahydroquinoline-3-carbonitrile; 4-(4-methoxyophenyl)-2-thioxo-1,2,5,6,7,8-hexahydroquinoline-3-carbonitrile; 4-(furan-2-yl)-2-thioxo-1,2,5,6,7,8-hexahydroquinoline-3-carbonitrile; and 4-(4-hydroxyphenyl)-2-thioxo-1,2,5,6,7,8-hexahydroquinoline-3-carbonitrile (see, e.g., Elgemeie et al., J. Carbohydrate Chem., 23: 465-481 (2004); Dyachenko V. D., Ukrainskii Ukrainskii Khimicheskii Zhurnal (Russian Edition), 74: 51-57 (2008); and Elnagdi et al., Tetrahedron, 45: 3597-3604 (1989)). The structures of the aforementioned pyridine thione compounds are set forth in Table 2.

In another embodiment, the substance that interferes with the activity of CUL4A is a 2,6-diamino-4-thiopyran-3,5-dicarbonitrile compound. The term "2,6-diamino-4-thiopyran-3,5-dicarbonitrile compound" refers to any compound which comprises at least one 2,6-diamino-4-thiopyran-3,5-dicarbonitrile moiety, and can also be referred to as a "2,6-diamino-4-thiopyran-3,5-dicarbonitrile-containing compound" or a "2,6-diamino-4-thiopyran-3,5-dicarbonitrile-based" compound. Any suitable 2,6-diamino-4-thiopyran-3,5-dicarbonitrile compound can be used in the inventive method. Suitable 2,6-diamino-4-thiopyran-3,5-dicarbonitrile compounds are known in the art, are commercially available, and include, for example, 2,6-diamino-4-(furan-2-yl)-4H-thiopyran-3,5-dicarbonitrile; 2,6-diamino-4-(5-bromo-2-fluorophenyl)-4H-thiopyran-3,5-dicarbonitrile; 2,6-diamino-4-(thiophen-2-yl)-4H-thiopyran-3,5-dicarbonitrile; 2,6-diamino-4-(quinolin-4-yl)-4H-thiopyran-3,5-dicarbonitrile; 2,6-diamino-4-(2-fluorophenyl)-4H-thiopyran-3,5-dicarbonitrile; 2,6-diamino-4-phenyl-4H-thiopyran-3,5-dicarbonitrile; 2,6-diamino-4-phenyl-4H-thiopyran-3,5-dicarbonitrile; 2,6-diamino-4-(2-nitrophenyl)-4H-thiopyran-3,5-dicarbonitrile; 2,6-diamino-4-(2,6-difluorophenyl)-4H-thiopyran-3,5-dicarbonitrile; 2,6-diamino-4-(3-fluorophenyl)-4H-thiopyran- 3,5-dicarbonitrile; 2,6-diamino-4-(2-(trifluoromethyl)phenyl)-4H-thiopyran-3,5-dicarbonitrile; 2,6-diamino-4-(pyridin-4-yl)-4H-thiopyran-3,5-dicarbonitrile; 2,6-diamino-4-(4-chlorophenyl)-4H-thiopyran-3,5-dicarbonitrile; 2,6-diamino-4-(4-methoxyphenyl)-4H-thiopyran-3,5-dicarbonitrile; 2,6-diamino-4-(furan-2-yl)-4H-thiopyran-3,5-dicarbonitrile; 2,6-diamino-4-(4-fluorophenyl)-4H-thiopyran-3,5-dicarbonitrile; and 6-diamino-4-(4-chlorophenyl)-2-mercapto-5-(piperidine-1carbonyl)nicotinonitrile (see, e.g., Fan et al., *J. Chem. Res.*, 12: 693-695 (2007) and U.S. Patent Application Publication No. 2009/0163545 A1). The structures of the aforementioned 2,6-diamino-4-thiopyran-3,5-dicarbonitrile compounds are set forth in Table 3.

In one embodiment, the substance that interferes with the activity of CUL4A is a 1,2,4-triazole-3-thiol compound. The term "1,2,4-triazole-3-thiol compound" refers to any compound which comprises at least one 1,2,4-triazole-3-thiol moiety, and can also be referred to as a "1,2,4-triazole-3-thiol-containing compound" or a "1,2,4-triazole-3-thiol-based" compound. Any suitable 1,2,4-triazole-3-thiol compound can be used in the inventive method. Suitable 1,2,4-triazole-3-thiol compounds are known in the art, are commercially available, and include, for example, 5-(4-methoxyphenyl)-4-(4-methylphenyl)-4H-1,2,4-triazole-3-thiol; 4-(3,4-dichlorophenyl)-5-(propan-2-yl)-4H-1,2,4-triazole-3-thiol; and 5-cyclopropyl-4-(3,4-dichlorophenyl)-4H-1,2,4-triazole-3-thiol. The structures of the aforementioned 1,2,4-triazole-3-thiol compounds are set forth in Table 4.

The substance that interferes with the activity of CUL4A can be a compound other than a 1,3-benzoxathiol-2-one compound, a pyridine thione compound, a 2,6-diamino-4-thiopyran-3,5-dicarbonitrile compound, or a 1,2,4-triazole-3-thiol compound. Examples of such substances include 3,3-dimethyl-8-(piperazin-1-yl)-6-sulfanylidene-1H,3H,4H, 6H,7H-pyrano[3,4-c]pyridine-5-carbonitrile; 3-bromo-5-methoxy-2,6-dinitropyridine; 10-thia-3,5,6,8-tetraazatetracyclo[7.7.0.0^{2,6}.0^{11,16}]hexadeca-1(9),2,4,11(16)-tetraen-7-one; 5-iodo-3-methoxy-1,2-thiazole-4-carbonitrile; [1-(6-chloro-5-nitropyrimidin-4-yl)piperidin-2-yl]methanol; 4,8-dichloro-[1,2,3,4]tetrazolo[1,5-a]quinoxaline; and methyl 4-amino-3-(2,4-difluorophenyl)-2-sulfanylidene-2,3-dihydro-3-thiazole-5-carboxylate. The structures of the aforementioned 1,3-benzoxathiol-2-one compounds are disclosed in Table 5.

The terms "preventing or treating," "treating," "treatment," "therapy," and "therapeutic treatment" as used herein refer to curative therapy, prophylactic therapy, or preventative therapy. An example of "preventative therapy" is the prevention or lessening of the chance of acquiring a cancer or other proliferative disease, or related condition thereto. Those in need of treatment include those animals already diagnosed with cancer as well as those animals prone to develop cancer. The terms "treating," "treatment," "therapy," and "therapeutic treatment" as used herein also describe the management and care of an animal for the purpose of combating cancer, or related condition, and includes the administration of a composition to alleviate the symptoms, side effects, or other complications of the cancer or related condition. The animal may be any animal, but preferably is a mammal. In one embodiment of the invention, the mammal is a mouse or other experimental mammal. In another embodiment, the mammal is a human.

The cancer may result from a tumor generally found in humans and other mammals or a tumor that arises as the result of inoculation, such as in experimental mammals. A tumor, as is known, includes an abnormal mass of tissue that results from uncontrolled and progressive cell division, and is also typically known as a "neoplasm." Many types of cancer are encountered in humans and animals, and the embodiments described herein are not limited to any particular cancer type. In this respect, the inventive method is useful for tumor cells and associated stromal cells, solid tumors, and tumors associated with soft tissue, such as, soft tissue sarcoma, for example, in a human. The tumor or cancer can be located in the skin (e.g., melanoma), oral cavity, pharynx, respiratory system, digestive system, bones, joints (e.g., bony metastases), soft tissue, breast, genital system, urinary system, eye, orbit, brain (e.g., glioma or medulloblastoma), central nervous system, or endocrine system (e.g., thyroid or adrenal gland) and is not necessarily the primary tumor or cancer. Tissues associated with the oral cavity include, but are not limited to, the tongue and tissues of the mouth. Cancer can arise in tissues of the digestive system including, for example, the esophagus, stomach, small intestine, colon, rectum, anus, liver, gall bladder, and pancreas. Cancers of the respiratory system can affect the larynx, lung, and bronchus and include, for example, non small cell lung carcinoma. Tumors can arise in the uterine cervix, uterine corpus, ovary vulva, vagina, prostate, testis, and penis, which make up the male and female genital systems, and the urinary bladder, kidney, renal pelvis, and ureter, which comprise the urinary system. The tumor or cancer can be located in the head and/or neck (e.g., laryngeal cancer and parathyroid cancer). The tumor or cancer also can be located in the hematopoietic system or lymphoid system, and include, for example, lymphoma (e.g., Hodgkin's disease and Non Hodgkin's lymphoma), multiple myeloma, or leukemia (e.g., acute lymphocytic leukemia, chronic lymphocytic leukemia, acute myeloid leukemia, chronic myeloid leukemia, and the like). Preferably, the tumor or cancer is located in the skin, breast, liver colon, brain, or adrenal gland. When the tumor or cancer is located in the brain, the tumor or cancer can be any known brain tumor or cancer, but preferably is a medulloblastoma. When the tumor or cancer is located in the adrenal gland, the tumor or cancer can be any known adrenal gland tumor or cancer, but is preferably an adrenocortical carcinoma.

By "effective amount" or "therapeutically effective amount," it is meant an amount that relieves (to some extent, as judged by a skilled medical practitioner) one or more symptoms of the cancer or related condition in an animal. Additionally, by "effective amount" or "therapeutically effective amount," it is meant an amount that returns to normal, either partially or completely, physiological or biochemical parameters associated with or causative of the cancer or related condition. A clinician skilled in the art can determine the therapeutically effective amount of a composition in order to treat or prevent a particular cancer when it is administered. The precise amount of the composition required to be therapeutically effective will depend upon numerous factors, e.g., such as the specific activity of the active substance, the delivery device employed, physical characteristics of the substance, purpose for the administration, in addition to many patient specific considerations. The determination of amount of a composition that must be administered to be an effective amount or a therapeutically effective amount is routine in the art and within the skill of an ordinarily skilled clinician.

By "administering" or "administered" it is meant that the substance is delivered to an animal in need thereof. The route of administration may be topical, oral, intranasal, parenteral, enteric, rectal, intravenous, intraperitoneal, subcutaneous, pulmonary, transdermal, intramuscular, buccal, sublingual, or ocular. The substance preferably is suitable for parenteral administration. The term "parenteral," as used herein, includes intravenous, intramuscular, subcutaneous, rectal, vaginal, and intraperitoneal administration. In one embodiment, the substance can be administered to a mammal using peripheral systemic delivery by intravenous, intraperitoneal, or subcutaneous injection.

The invention also provides a composition comprising (a) the substance that interferes with the activity of CUL4A and (b) a carrier. The carrier typically will be liquid, but also can be solid, or a combination of liquid and solid components. The carrier desirably is physiologically acceptable (e.g., a pharmaceutically, pharmacologically, or cosmetically acceptable) carrier (e.g., excipient or diluent). Any suitable physiologically acceptable carrier can be used within the context of the invention, and such carriers are well known in the art. The choice of carrier will be determined, at least in part, by the location of the target tissue and/or cells, and the particular method used to administer the composition.

The composition can further comprise any other suitable components, especially for enhancing the stability of the composition and/or its end use. Accordingly, there is a wide variety of suitable formulations of the composition of the invention. The following formulations and methods are merely exemplary and are in no way limiting.

Formulations suitable for parenteral administration include aqueous and non aqueous, isotonic sterile injection solutions, which can contain anti oxidants, buffers, bacteriostats, and solutes that render the formulation isotonic with the blood of the intended recipient, and aqueous and non aqueous sterile suspensions that can include suspending agents, solubilizers, thickening agents, stabilizers, and preservatives. The formulations can be presented in unit dose or multi dose sealed containers, such as ampules and vials, and can be stored in a freeze dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described. The formulation for parenteral administration can be formulated for intratumoral administration, intravenous injection, intraperitoneal injection, intraocular injection, subcutaneous injection, and the like.

Compositions suitable for enteric administration are formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient. Pharmaceutical preparations for oral use can be obtained through combining active compounds with solid excipients, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as cross-linked polyvinyl pyrrolidone, agar, alginic acid, or a salt thereof, such as sodium alginate. Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Formulations suitable for anal or rectal administration can be prepared as suppositories by mixing the active substance with a variety of bases such as emulsifying bases or water soluble bases. Formulations suitable for vaginal administration can be presented as pessaries, tampons, creams, gels, pastes, foams, or spray formulas containing, in addition to the active ingredient, such carriers as are known in the art to be appropriate.

Formulations suitable for ocular administration can be prepared as an injectables, drops, sprays, or films, by mixing the active substance with a variety of aqueous and non aqueous, isotonic sterile injection solutions, which can contain anti-oxidants, buffers, bacteriostats, and solutes that render the formulation isotonic with the eye tissue of the intended recipient, and aqueous and non aqueous sterile suspensions that can include suspending agents, solubilizers, thickening agents, stabilizers, and preservatives.

Formulations suitable for topical administration include creams, lotions, ointments, patches, oils, pastes, sprays (e.g., an aerosol spray), gels, mousse, roll-on liquids, solid sticks, etc. Preferably, the topical formulation of the invention is a cream, a lotion, an ointment, or a patch.

In one embodiment of the invention, the substance that interferes with the activity of CUL4A, alone or in combination with other suitable components, is made into an aerosol formulation to be administered via inhalation. A substance of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used, e.g., to spray mucosa and may be particularly preferable for preventing or treating cancers of the respiratory system or the oral cavity and pharynx.

In another embodiment, the formulation is a sunscreen composition comprising the substance that interferes with the activity of CUL4A and a cosmetically acceptable carrier. Typically, a sunscreen composition is an oil-in-water or water-in-oil emulsion wherein the oil phase comprises one or more sunscreen compounds, solubilizers, silicone emulsifiers, emollients, and other cosmetically acceptable skin conditioning agents. The aqueous phase is predominantly water, but typically comprises additional ingredients such as humectants (e.g., pentylene glycol and glycerine), preservatives, and thickeners. Additional components such as fragrances, dyes, and extracts may be added to either phase or to the emulsion after it is prepared. Similarly, the substance that interferes with the activity of CUL4A of the invention may be added to the oil phase, the aqueous phase, or the emulsion after it is prepared depending upon the physiochemical characteristics of the substance.

The term "sunscreen compound" refers to a compound capable of screening ultraviolet radiation having a wavelength of 280 nm-320 nm (i.e., UV-B) and/or 320 nm-400 nm (i.e., UV-A). The sunscreen compound may be one or more organic chemicals that absorb UV radiation, one or more inorganic chemicals that reflect, scatter, or absorb UV radiation, or any combination thereof. Examples of suitable sunscreen compounds include, without limitation, sulisobenzone, dioxybenzone, methyl anthranilate, 4-aminobenzoic acid (PABA), amyl dimethyl PABA, octyl dimethyl PABA, glyceryl PABA, 2-ethoxyethyl p-methoxycinnamate, diethamolamine p-methoxycinnamate, ethylhexyl p-methoxycinnamate, digalloyl trioleate, ethyl 4-bis (hydroxypropyl) aminobenzoate, 2-ethylhexyl-2-cyano-3,3-diphenylacrylate, 2-ethylhexyl salicylate, homomenthyl salicylate, triethanolamine salicylate, 2-phenylbenzimidazole-5-sulfonic acid, red petrolatum, titanium dioxide, zinc oxide, and combinations thereof.

The sunscreen composition can take the form of a lotion, an oil, a gel, a solid stick, a spray, or a foam. Sunscreen compositions and methods of preparation are well known to one of ordinary skill in the art and are described in, e.g., U.S. Pat. Nos. 5,587,150; 5,770,183; and 6,033,649.

The invention provides a method of co-administering a substance that interferes with the activity of CUL4A with a sunscreen composition to an animal in need thereof. By "co-administering" is meant administering the sunscreen composition and the substance that interferes with the activity of CUL4A sufficiently close in time such that the substance that interferes with the activity of CUL4A can enhance the effectiveness of the sunscreen composition. In this regard, the substance that interferes with the activity of CUL4A can be administered first and the sunscreen composition can be administered second, or vice versa. Alternatively, the substance that interferes with the activity of CUL4A and sunscreen composition can be administered simultaneously.

The invention also provides a method of co-administering a substance that interferes with the activity of CUL4A with a chemotherapeutic agent to an animal in need thereof. By "co-administering" is meant administering the chemotherapeutic agent and the substance that interferes with the activity of CUL4A sufficiently close in time such that the substance that interferes with the activity of CUL4A can enhance the effectiveness of the chemotherapeutic agent. In this regard, the substance that interferes with the activity of CUL4A can be administered first and the chemotherapeutic agent can be administered second, or vice versa. Alternatively, the substance that interferes with the activity of CUL4A and the chemotherapeutic agent can be administered simultaneously.

Any class of chemotherapeutic agent can be co-administered with the substance that interferes with the activity of CUL4A, including without limitation, an antimicrotubule agent, an antimetabolite, an antimitotic, a DNA damaging agent, a proapoptotic, a differentiation inducing agent, an antibiotic, a hormone, and any combination thereof. Suitable chemotherapeutics include, but are not limited to, tyrosine kinase inhibitors (genistein), biologically active agents (TNF, or tTF), radionuclides (131I, 90Y, 111In, 211At, 32P and other known therapeutic radionuclides), adriamycin, ansamycin antibiotics, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, meplhalan, methotrexate, rapamycin (sirolimus) and derivatives, mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxol, combretastatins, discodermolides, transplatinum, anti vascular endothelial growth factor compounds ("anti VEGFs"), anti epidermal growth factor receptor compounds ("anti EGFRs"), 5 fluorouracil, and the like. A dose of one or more chemotherapeutic agents can be administered according to the inventive method. The type and number of chemotherapeutic agents used in the inventive method will depend on the standard chemotherapeutic regimen for a particular tumor type. In other words, while a particular cancer may be treated routinely with a single chemotherapeutic agent, another may be treated routinely with a combination of chemotherapeutic agents. The chemotherapeutic agent is administered in a dose sufficient to treat the cancer (e.g., cancer-treatment effective amount of a chemotherapeutic agent). A clinician skilled in the art can determine the therapeutically effective amount of a composition in order to treat or prevent a particular disease condition, or disorder when it is administered.

The following examples further illustrate the invention but, of course, should not be construed as in any way limiting its scope.

EXAMPLE 1

This example demonstrates a high-throughput screening (HTS) assay for identifying a substance that interferes with (e.g., inhibits) CUL4A binding to DDB1.

X-ray crystallographic studies have revealed the molecular details of the DDB1-CUL4A association (Angers et al., *Nature*, 443: 590-593 (2006); Li et al., *Cell*, 124: 105-117 (2006)). Eight residues within the DDB1-BPB β-propeller region (A400, I402, L404, V443, E537, W561, I587, and R589) were identified to form direct contacts with CUL4A. Both DDB1 and CUL4A contain multiple modular domains for protein-protein interactions that mediate assembly of other E3 components and additional regulators. To direct the selection of inhibitors of the CUL4A ubiquitin ligase, a bead-based non-radioactive Amplified Luminescent Proximity Homogeneous Assay (ALPHALISA™) was established to screen for small molecule inhibitors that abrogate the interaction between the BPB domain of DDB1 and the CUL4A/Rbx1 heterodimer either competitively or allosterically. To apply the ALPHALISA™ system (PerkinElmer, Waltham, Mass.), donor beads coupled with anti-GST antibody were used to capture GST-CUL4A, and acceptor beads that bind the FLAG tag were used to immobilize FLAG-DDB1(BPB). The proximity of donor to acceptor beads was induced upon binding of CUL4A to DDB1(BPB), resulting in the generation of luminescent signal at 520 nm upon excitation at 680 nm, as recorded by an ENVISION™ Multilabel Plate Reader (PerkinElmer, Waltham, Mass.). The ALPHALISA™ binding assay was performed in 384-well microplates in triplicate, and compounds eliciting ≥70% inhibition in signal strength were defined as "hits."

The parameters measured in the CUL4A(NTD-N)-DDB1 (BPB) binding assay include, for example, binding affinity, binding specificity, vehicle (i.e., DMSO) sensitivity. $IC_{50}$, and signal/background ratio. The assay conditions are described in detail in, e.g., U.S. Pat. No. 8,513,181.

Small molecule libraries containing about ~64,000 compounds were screened at the Rockefeller University HTS core facility. 352 compounds were identified based on the 70% inhibition of ALPHALISA™ signal and at 15 µM concentration of compounds. Hit compounds were re-tested on the above-described HTS platform for dose-dependent inhibition of the ALPHALISA™ signal with the hit compounds, and for measurement of $IC_{50}$. The TruHits assay (PerkinElmer, Waltham, Mass.) was used to determine "false positive" compounds that non-specifically inhibit the ALPHALISA™ signal. Two additional small molecule compounds were separately generated and tested as described above. Specifically, 2,6-diamino-4-(2,6-difluorophenyl)-4H-thiopyran-3,5-dicarbonitrile was synthesized as follows: to a solution of malononitrile (66 mg, 1.0 mmol), 2,6 difluorobenzaldehyde (142 mg, 1.0 mmol), and piperidine (8.5 mg, 10 µL, 0.1 mmol) in absolute ethanol (15 mL) was added 2-cyanothioacetamide (100 mg, 1.0 mmol). The resulting brown solution stirred for three hours at room temperature, at which point water (40 mL) was added and a yellow precipitate formed. The precipitate was isolated by filtration, washed with water and hexane, then dried in vacuo to provide 2,6-diamino-4-(2,6-difluorophenyl)-4H-thiopyran-3,5-dicarbonitrile as a yellow solid (183 mg, 0.63 mmol, 63%). 1H NMR (500 MHz, DMSO-d6) δ 7.41 (dddd, J=8.5, 8.5, 6.1, 6.1), 7.12 (m, 2H), 6.94 (s, 4H), 4.81 (s, 1H). 2,6-diamino-4-(4-chlorophenyl)-4H-thiopyran-3,5-dicarbonitrile was produced as follows: to a solution of malononitrile (132 mg, 2.0 mmol), 4-chlorobenzaldehyde (281 mg, 2.0 mmol), and piperidine (20 µL, 0.2 mmol) in absolute ethanol (20 mL) was added 2-cyanothioacetamide (200 mg, 2.0 mmol). The resulting solution stirred for three hours at room temperature, at which point water (50 mL) was added and a yellow precipitate formed. The precipitate was isolated by filtration, washed with water and hexane, then dried in vacuo to provide 2,6-diamino-4-(4-chlorophenyl)-4H-thiopyran-3,5-dicarbonitrile as a yellow solid (354 mg, 1.23 mmol, 61%). 1H NMR (500 MHz, DMSO-d6) δ 7.43 (d, J=8.2 Hz, 2H), 7.26 (d, J=8.2 Hz, 2H), 6.98 (s, 4H), 4.32 (s, 1H).

In total, 48 compounds were identified with an $IC_{50}$ of less than 5 µM.

Based on the chemical structures of the small molecules tested, four major chemotypes were identified: (I) 1,3-benzoxathiol-2-one-containing compounds, (II) pyridine thione-containing compounds, (III) 2,6-diamino-4-thiopyran-3,5-dicarbonitrile-containing compounds, and (IV) 1,2,4-triazole-3-thiol-containing compounds. The structures of these compounds are set forth in FIGS. 7-10. A collection of individual compounds with unique chemical structures also were identified or synthesized as described above, the structures of which are set forth in FIG. 11.

Compounds that were commercially available were purchased and subjected to an assay for inhibition of CUL4A ubiquitin ligase activity. The assay is an in vitro ubiquitination assay to examine whether the hit compounds inhibit a reconstituted DDB1 ubiquitination reaction that includes affinity-purified ubiquitin, E1, E2, CUL4A/Rbx1 and DDB1. Specifically, ubiquitin enzyme E1, E2 (UbcH5B), E3 (GST-CUL4-Rbx1), substrate (GST-DDB1) and ubiquitin protein were mixed in Ub assay buffer containing DMSO or s hit compound. After a one-hour incubation at 25° C., the reactions were terminated by boiling in 5×SDS loading buffer for five minutes. The DDB1 Ub ladder was detected by Western blotting using the anti-DDB1 antibody. The results of the CUL4A ubiquitin ligase assay are shown in FIG. 1.

Figure 2:
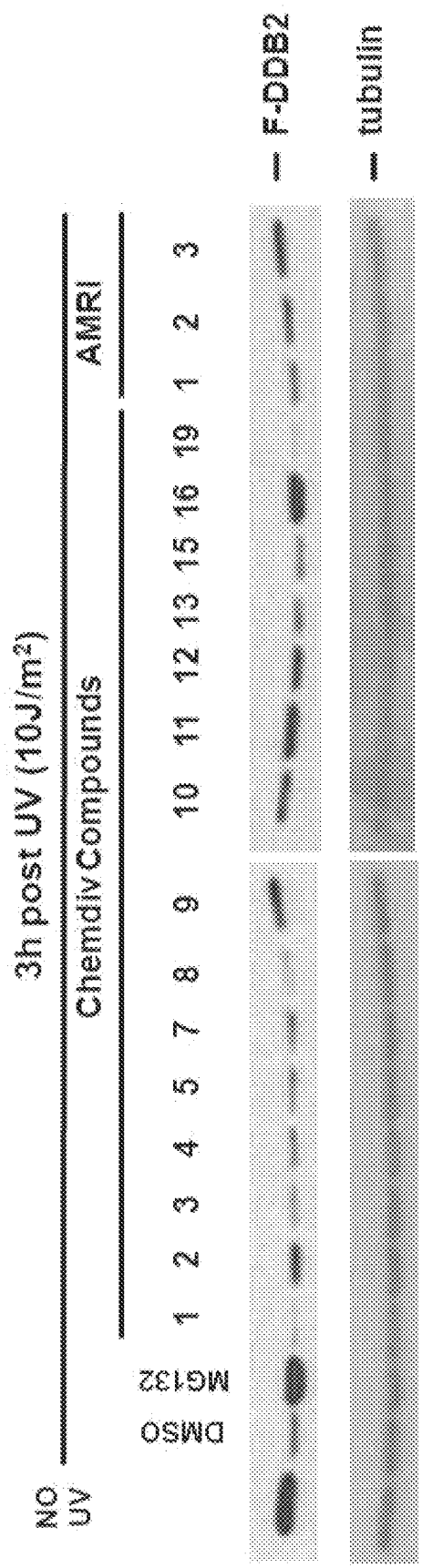
Figure 3:
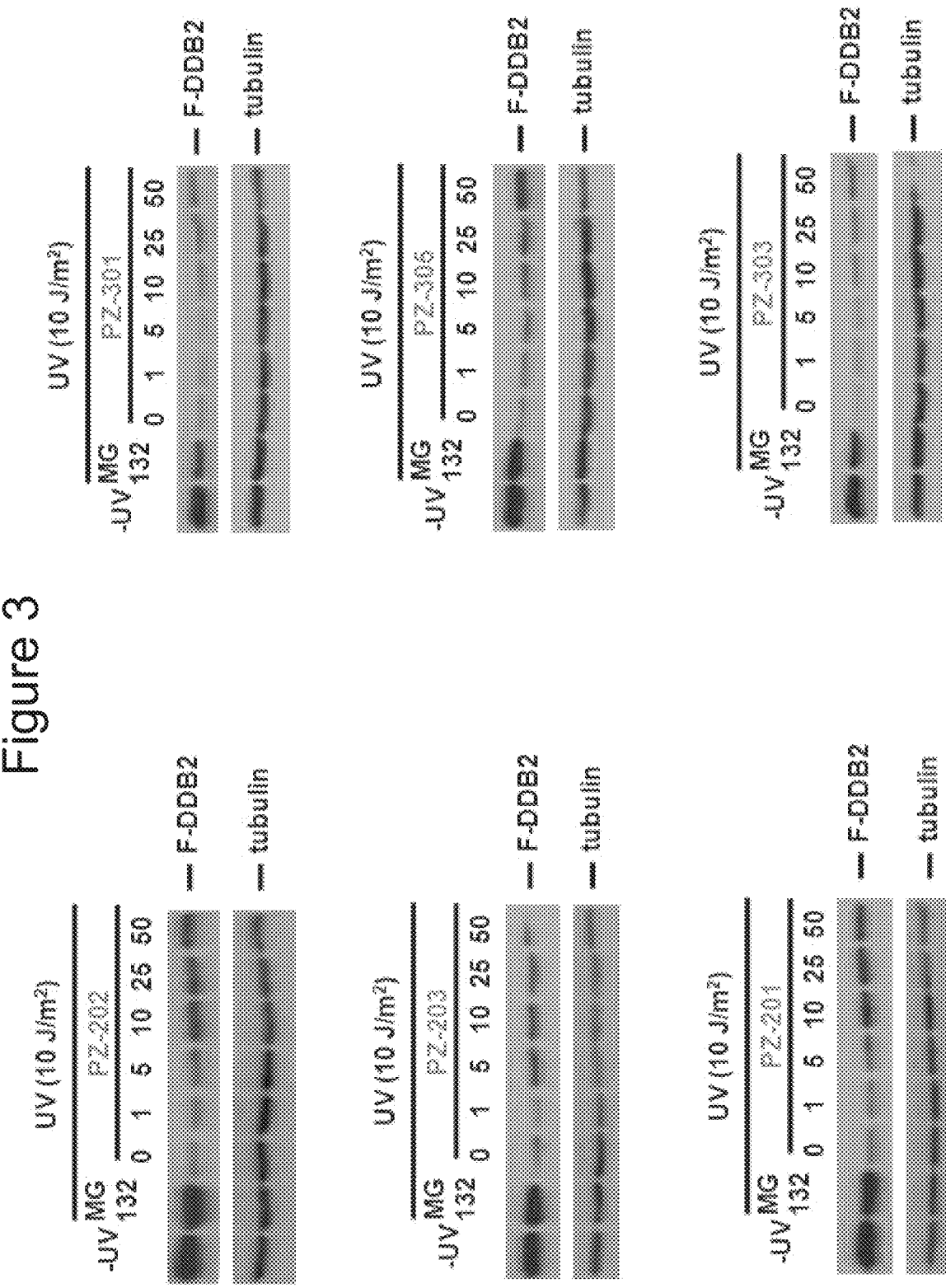

A cell-based assay for DDB2 degradation by CUL4A following exposure to UV light was used as a second validation assay to evaluate the hit compounds. As discussed herein, DDB2 is an established substrate of the CUL4A ubiquitin ligase. Mouse embryonic fibroblast (MEF) cells stably expressing a FLAG-tagged DDB2 were irradiated with UV (10 J/m$^2$) following a two-hour incubation with DMSO or hit compounds. Three hours post UV exposure, cells were lysed in 1×SDS buffer and protein concentrations were measured by the BCA kit. F-DDB2 levels were detected by SDS PAGE and Western blotting, and tubulin levels were used as loading control. A FLAG-tagged version of DDB2 (designated F-DDB2) was rapidly degraded by CUL4A upon UV irradiation in MEFs. MG132, which is a proteasome inhibitor that blocks UV-induced DDB2 degradation was used a positive control (see FIG. 2, lane 3). The results of this assay are shown in FIG. 2. Small molecule compounds from the different chemotype groups identified above showed either significant or partial inhibition of CUL4A E3 activity in this assay. The assay was repeated for certain pyridine thione-containing compounds and 2,6-diamino-4-thiopyran-3,5-dicarbonitrile-containing compounds to determine if the compounds could inhibit CUL4A ubiquitin ligase in a dose-dependent manner. The results of this assay are shown in FIG. 3. All six compounds tested displayed dose-dependent inhibition of F-DDB2 degradation by CUL4A following UV irradiation.

Figure 4:
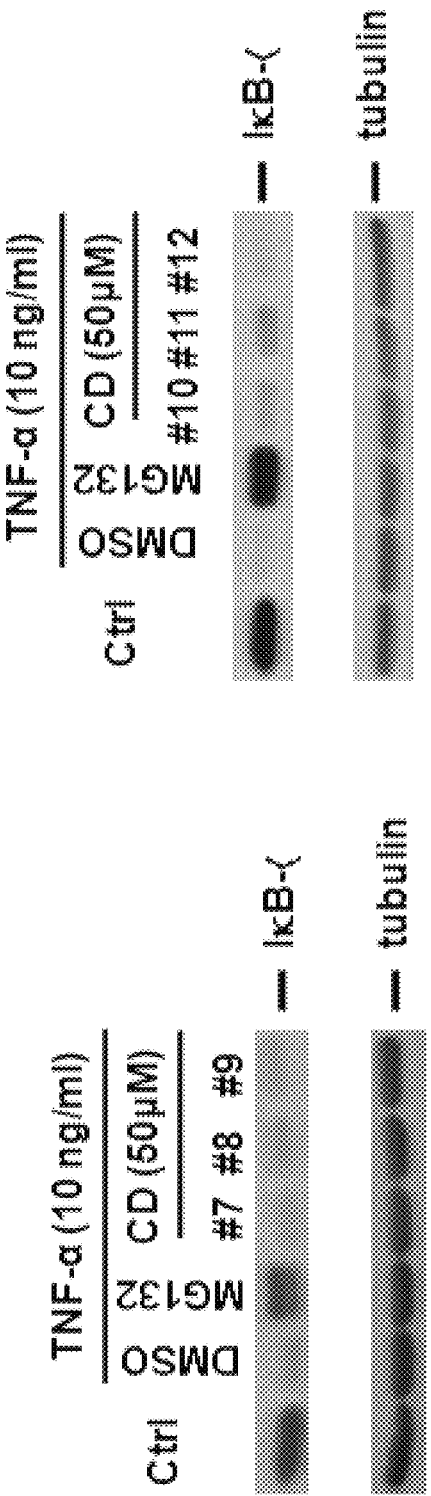
Figure 5:
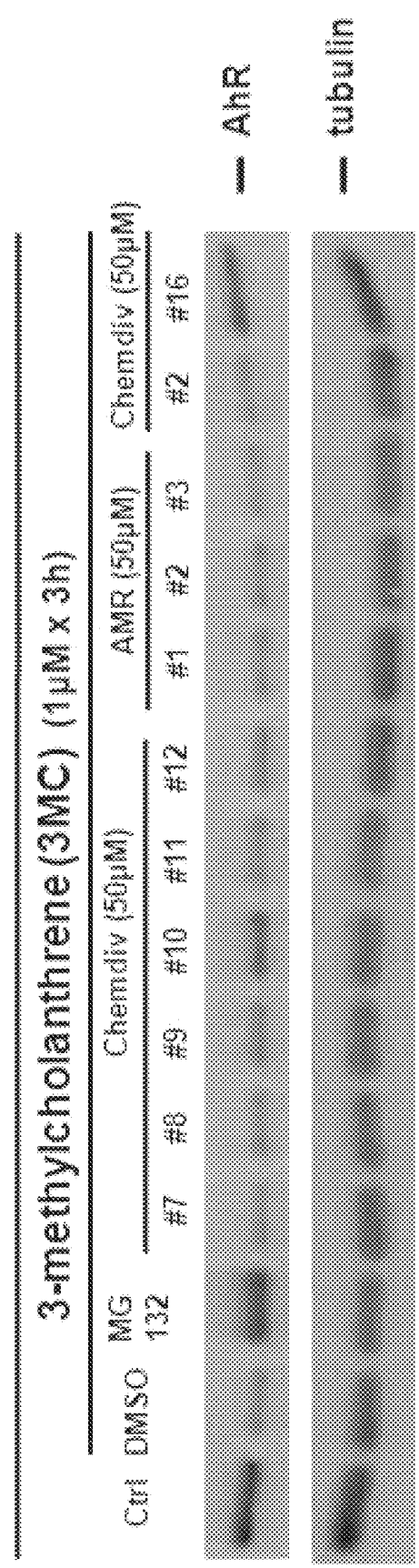

The specificity of certain pyridine thione-containing compounds and 2,6-diamino-4-thiopyran-3,5-dicarbonitrile-containing compounds for CUL4A was tested in MEFs by measuring TNF-α-induced degradation of IκB-α, which is an established substrate of the CUL1 ubiquitin ligase (see e.g. Kretz-Remy et al., *J. Cell. Biol.*: 133(5):1083-1093 (1996)). Specifically, U2OS cells were incubated with DMSO or hit compounds for two hours, and then were treated with TNF-α (10 ng/ml) for 15 minutes. Cells were lysed in 1×SDS buffer and protein concentrations were measured by the BCA kit. IκB-α levels were determined by Western blot, and tubulin levels were used as loading control. The results of this assay are shown in FIG. 4. The tested compounds exhibited no inhibition of CUL-1 dependent IκB-α turnover. A cell-based AhR degradation assay also was performed to confirm specificity of the small molecule compounds. The aryl hydrocarbon receptor (AhR) which is a close family member of CUL4A. Upon exposure to environmental toxins, CUL4B assembles a distinct E3 ubiquitin ligase with dioxin-bound aryl hydrocarbon receptor (AhR), which targets AhR itself, as well as estrogen receptor and progesterone receptor for ubiquitination and degradation (see, e.g., Kato et al., *Nature*, 446(7135): 562-566 (2007)). MCF-7 cells were incubated with DMSO or hit compounds for two hours, treated with 1 µM 3-methylcholanthrene (3-MC) for three hours, and lysed in 1×SDS buffer. Protein concentrations were measured by the BCA kit. AhR levels were detected by Western blot, and α-tubulin levels were used as loading control. The results of this assay are shown in FIG. 5. MCF-7 cell treated with 3-methylcholanthrene (3-MC) exhibited rapid degradation of endogenous AhR (FIG. 5, lanes 1 and 2). MG132 was used a positive control. 3-MC administration induced CUL4B-dependent AhR turnover, and the hit compounds had no effect on CUL4B-dependent AhR degradation. The results of the specificity assays strongly suggest that the hit compounds specifically target the CUL4A ubiquitin ligase.

The results of this example demonstrate the identification of small molecules that interfere with the activity of CUL4A.

EXAMPLE 2

This example demonstrates the ability of a substance that interferes with the activity of CUL4A, thereby promoting repair of DNA damage induced by UV radiation.

Figure 6:
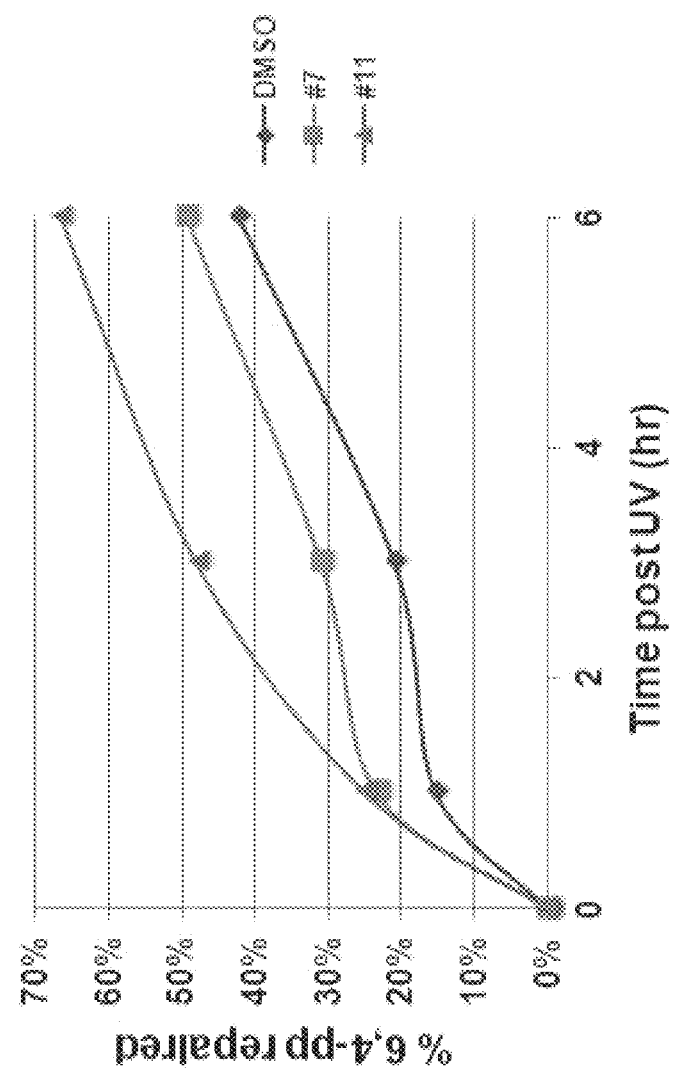
FIG. 6 is a graph which depicts experimental data illustrating the rate of repair of 6,4-photoproducts (6,4-PPs) in HTC116 cells treated with the hit compounds PZ-202 and PZ-305 following exposure to UV radiation. Control MEF cells treated with DMSO vehicle ("DMSO") served as a control.

CUL4A inactivation, either through gene knockout or RNAi knockdown, has been shown to prevent DDB2 degradation by CUL4A, thereby increasing nucleotide excision repair (NER) activity (see, e.g., U.S. Patent Application Publication No. 2011/0044921 and Liu et al., *Mol. Cell.*, 34(4): 451-60 (2009)). Human HCT116 colon cancer cells are established model cells that were used to test the effects of the CUL4A inhibitors described in Example 1 on DDB2 degradation and to measure the effects on NER activity. HCT116 cells were UV-irradiated following incubation with certain hit compounds identified in Example 1 or DMSO for two hours. The irradiated cells were harvested at time points indicated in FIG. 6 and total genomic DNA was extracted with the DNeasy kit (Qiagen, Venlo, The Netherlands). UV-induced 6,4-photoproducts (6,4-pp) were detected by ELISA assay with an anti-6,4-pp monoclonal antibody (see, e.g., Chen et al., *Mol. Cell.*, 22(4): 489-99 (2006), and U.S. Patent Application Publication No. 2011/0044921). The results of this assay are shown in FIG. 6.

Compared to the control MEF cells (labeled "DMSO"), addition of compound #7 (PZ-202) or compound #11 (PZ-305) both led to enhanced removal of 6,4-photoproducts. Therefore, the results of this example demonstrate that the small molecule CUL4A inhibitors described herein can promote the repair of UV-damaged DNA.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a CUL4A overexpressing cancer in an animal, which method comprises interfering with the activity of CUL4A in the animal by administering to the animal an effective amount of a substance that interferes with the activity of CUL4A, wherein the substance is 2,6-diamino-4-(furan-2-yl)-4H-thiopyran-3,5-dicarbonitrile; 2,6-diamino-4-(5-bromo-2-fluorophenyl)-4H-thiopyran-3,5-dicarbonitrile; 2,6-diamino-4-(thiophen-2-yl)-4H-thiopyran-3,5-dicarbonitrile; 2,6-diamino-4-(quinolin-4-yl)-4H-thiopyran-3,5-dicarbonitrile; 2,6-diamino-4-(2-fluorophenyl)-4H-thiopyran-3,5-dicarbonitrile; 2,6-diamino-4-phenyl-4H-thiopyran-3,5-dicarbonitrile; 2,6-diamino-4-phenethyl-4H-thiopyran-3,5-dicarbonitrile; 2,6-diamino-4-(2-nitrophenyl)-4H-thiopyran-3,5-dicarbonitrile; 2,6-diamino-4-(2,6-difluorophenyl)-4H-thiopyran-3,5-dicarbonitrile; 2,6-diamino-4-(2-(trifluoromethyl)phenyl)-4H-thiopyran-3,5-dicarbonitrile; 2,6-diamino-4-(pyridin-4-yl)-4H-thiopyran-3,5-dicarbonitrile; 2,6-diamino-4-(4-chlorophenyl)-4H-thiopyran-3,5-dicarbonitrile; 2,6-diamino-4-(4-methoxyphenyl)-4H-thiopyran-3,5-dicarbonitrile; 2,6-diamino-4-(furan-2-yl)-4H-thiopyran-3,5-dicarbonitrile; or 2,6-diamino-4-(4-fluorophenyl)-4H-thiopyran-3,5-dicarbonitrile wherein the CUL4A overexpressing cancer is a CUL4A overexpressing skin cancer, a CUL4A overexpressing breast cancer, a CUL4A overexpressing liver cancer, a CUL4A overexpressing colon cancer, a CUL4A overexpressing adrenocortical carcinoma, or a CUL4A overexpressing brain cancer; thereby treating the CUL4A overexpressing cancer in the animal.

2. The method of claim 1, wherein the substance that interferes with the activity of CUL4A is administered topically, orally, intranasally, parenterally, enterically, rectally, or ocularly.

3. The method of claim 1, wherein the substance that interferes with the activity of CUL4A is administered in a composition comprising the substance and a carrier.

4. The method of claim 1, further comprising administering a chemotherapeutic agent to the animal.

5. The method of claim 4, wherein the chemotherapeutic agent is selected from the group consisting of antimicrotubule agents, antimetabolites, antimitotics, DNA damaging agents, proapoptotics, differentiation inducing agents, antibiotics, and hormones.

6. The method of claim 1, wherein the animal is a mammal.

7. The method of claim 6, wherein the mammal is a human.

8. The method of claim 1, wherein the CUL4A overexpressing cancer is a CUL4A overexpressing breast cancer.

9. The method of claim 1, wherein the CUL4A overexpressing cancer is a CUL4A overexpressing colon cancer.

* * * * *